(12) United States Patent
Tan et al.

(10) Patent No.: US 10,683,517 B2
(45) Date of Patent: *Jun. 16, 2020

(54) CRY1D FOR CONTROLLING CORN EARWORM

(71) Applicant: AGRIGENETICS, INC., Indianapolis, IN (US)

(72) Inventors: Sek Yee Tan, Carmel, IN (US); Joel J. Sheets, Zionsville, IN (US); Todd Glancy, Fairmount, IN (US); Aaron T. Woosley, Fishers, IN (US); Sarah E. Worden, Fillmore, IN (US); Diaa Alabed, Carmel, IN (US); Stephanie Burton, Indianapolis, IN (US); Karen C. McLaughlin, Indianapolis, IN (US); Kenneth E. Narva, Zionsville, IN (US); Thomas Meade, Zionsville, IN (US)

(73) Assignee: AGRIGENETICS, INC. IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/894,267

(22) Filed: Feb. 12, 2018

(65) Prior Publication Data

US 2018/0163224 A1 Jun. 14, 2018

Related U.S. Application Data

(63) Continuation of application No. 14/664,307, filed on Mar. 20, 2015, now Pat. No. 9,890,390.

(60) Provisional application No. 61/968,703, filed on Mar. 21, 2014.

(51) Int. Cl.
*C12N 15/82* (2006.01)
*A01N 63/02* (2006.01)
*C07K 14/325* (2006.01)

(52) U.S. Cl.
CPC ......... *C12N 15/8286* (2013.01); *A01N 63/02* (2013.01); *C07K 14/325* (2013.01); *Y02A 40/162* (2018.01)

(58) Field of Classification Search
None
See application file for complete search history.

(56) References Cited

U.S. PATENT DOCUMENTS

| 7,511,129 B2 | 3/2009 | Payne et al. |
| 8,304,604 B2 * | 11/2012 | Lira ..................... C07K 14/325 |
| | | 800/279 |
| 9,890,390 B2 * | 2/2018 | Tan ........................ A01N 63/02 |
| 2006/0112447 A1 | 5/2006 | Bogdanova et al. |
| 2010/0221238 A1 | 9/2010 | Flexner et al. |
| 2010/0235951 A1 | 9/2010 | Van Rie et al. |
| 2012/0331589 A1 * | 12/2012 | Meade .................. A01N 63/02 |
| | | 800/302 |
| 2013/0025006 A1 | 1/2013 | Meade et al. |

FOREIGN PATENT DOCUMENTS

| WO | 2000/026371 | 11/2000 |
| WO | 2011/084629 | 7/2011 |
| WO | 2011/084630 | 7/2011 |
| WO | 2014/055881 | 4/2014 |
| WO | 2016/061377 | 4/2016 |

OTHER PUBLICATIONS

Capinera (2005, http://entnemdept.ufl.edu/creatures/field/ fall_armyworm.htm).*
Capinera (2017, http://entnemdept.ufl.edu/ creatures/veg/corn_earworm.htm).*
Lynch, et al., "Evaluation of Transgenic Sweet Corn Hybrids Expressing Cry1A(b) Toxin for Resistance to Corn Earworm and Fall Armyworm (Lepidoptera: Noctuidae)," Journal of Economic Entomology, Feb. 1, 1999 (Feb. 1, 1999), vol. 92, Issue 1, pp. 246-252.
International Search Report and Written Opinion prepared for PCT/US2015/021734, dated Jul. 8, 2015, 8 pages.

* cited by examiner

*Primary Examiner* — Anne Kubelik

(57) ABSTRACT

The subject invention relates in part to the surprising discovery that Cry1Da is active against corn earworm (CEW), *Helicoverpa zea* (Boddie). Methods for using Cry1Da in transgenic plants to prevent serious crop damage is described. Leaf and silk bioassays using transgenic maize expressing full length, core toxin region or chimeric Cry1Da demonstrated good insect protection against CEW larvae damage.

14 Claims, 1 Drawing Sheet
Specification includes a Sequence Listing.

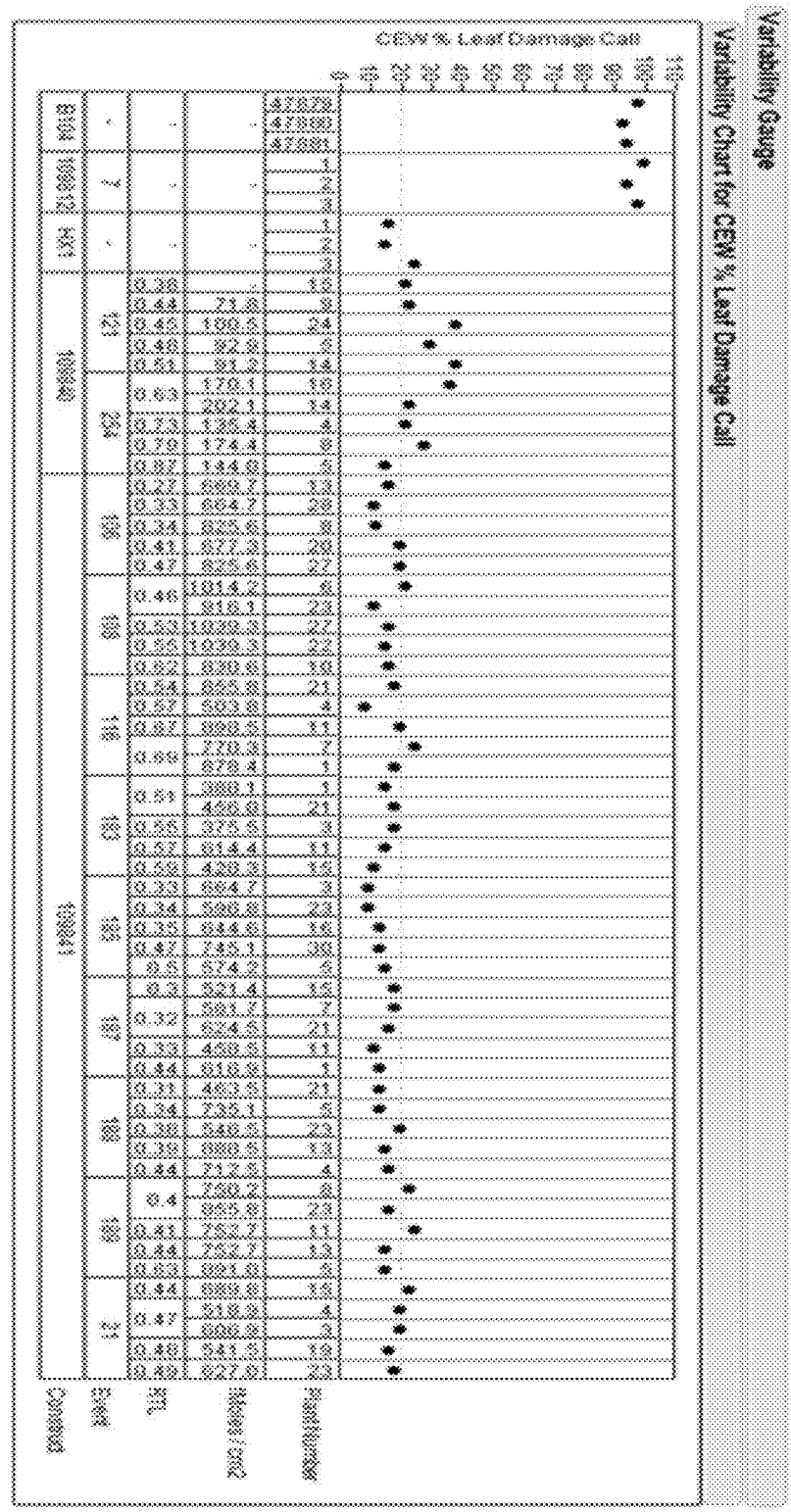

CRY1D FOR CONTROLLING CORN EARWORM

CROSS REFERENCE

This application is a continuation of U.S. patent application Ser. No. 14/664,307, filed on Mar. 20, 2015 and now issued as U.S. Pat. No. 9,890,390, which claims the benefit of U.S. Provisional Application No. 61/968,703, filed on Mar. 21, 2014, the disclosures of which are expressly incorporated by reference herein in their entirety.

SEQUENCE LISTING

The instant application contains a Sequence Listing which has been submitted electronically in ASCII format and is hereby incorporated by reference in its entirety. Said ASCII copy, created on Feb. 12, 2018, is named 275208-ST25.txt and is 39,225 bytes in size.

BACKGROUND

Cry1Da is a known delta-endotoxin produced by certain species of *Bacillus thuringiensis* and was first described in U.S. Pat. No. 5,691,308. More recently has been reported to be inactive against corn earworm (CEW) by two independent peer reviewed papers: Karim et al. (2000) and Frankenhuyzen (2009). Consequently the following surprising and unexpected observations directly refutes these published results and clearly shows that Cry1Da has good insecticidal activity against CEW larvae when the gene is expressed in plants.

BRIEF SUMMARY

The subject invention relates in part to the surprising discovery that Cry1Da is active against corn earworm larvae (CEW), *Helicoverpa zea* (Boddie). Leaf and silk bioassays using transgenic maize expressing a full length, truncated, and chimeric versions of Cry1Da demonstrated good insect protection against CEW larvae damage. Further surprising was that protection of CEW larvae feeding of maize silk was found to be superior in transgenic plants expressing truncated Cry1Da as compared to commercial plants producing Cry1Fa.

CEW is a difficult insect pest to control with *Bacillus thuringiensis* (Bt) proteins, and this is the first described observation where transgenic maize expressing Cry1Da demonstrated biological activity to protect maize silk from feeding damage caused by this insect. Adult CEW moths typically oviposite their eggs on corn silk, and the newly emerging larvae feed on corn silk prior to entering the ear. Thus, having insect protectant activity located in maize silk tissues will provide significant protective effects against feeding damage caused by this significant and destructive pest of maize.

BRIEF DESCRIPTION OF THE FIGURE

Percent leaf damage activity of non-transformed maize (B-104), YFP expressing transgenic maize (109812), HerculexI™ maize (HX1), or transgenic T-1 maize expressing either full length Cry1Da (109840), or truncated Cry1Da (109841) challenged with CEW larvae.

BRIEF DESCRIPTION OF THE SEQUENCES

SEQ ID NO: 1 is a DNA fragment having the DIG-911 coding sequence (CDS)

SEQ ID NO:2 is the amino acid sequence for the DIG-911 protein (Cry1Da2/Cry1Ab chimeric insecticidal toxin, which consists of a core toxin segment of Cry1Da (amino acids 1 to 594, as disclosed in GENBANK Accession No. 176415.1 and U.S. Pat. No. 5,691,308) and a protoxin segment derived from Cry1Ab (DIG-911 amino acids 595 to 1139), essentially as disclosed in GENBANK Accession No. AFK79795.1)

SEQ ID NO:3 is a DNA fragment having the DIG-180 coding sequence (CDS)

SEQ ID NO:4 is the DIG-180 (Cry1Fa2) protein.

SEQ ID NO:5 is a Gateway® (INVITROGEN) entry vector pDAB109825 comprising a maize-optimized coding sequence (SEQ ID NO:5) that encodes a Cry1Da2 core toxin insecticidal protein (SEQ ID NO:6).

SEQ ID NO:6 is the Cry1Da2 core toxin insecticidal protein.

SEQ ID NO:7 is a primer for AAD-1; see Table 2

SEQ ID NO:8 is a primer for AAD-1

SEQ ID NO:9 is a probe for AAD-1

SEQ ID NO:10 is a primer for the spectinomycin resistance gene

SEQ ID NO:11 is a primer for the spectinomycin resistance gene

SEQ ID NO:12 is a probe for the spectinomycin resistance gene

SEQ ID NO:13 is a primer for the maize invertase gene

SEQ ID NO:14 is a primer for the maize invertase gene

SEQ ID NO: 15 is a probe for the maize invertase gene

DETAILED DESCRIPTION

The subject invention relates in part to the surprising discovery that Cry1Da is active against corn earworm larvae (CEW), *Helicoverpa zea* (Boddie). Bioassay results from in vitro diet bioassays showed Cry1Da/Cry1Ab protoxin chimera results in significant growth inhibition and mortality to CEW larvae. A Cry1Da insecticidal protein or toxin is any insecticidal protein comprising the core toxin set forth in SEQ ID NO:6 or variants thereof. Such variants have at least 95% sequence identity to SEQ ID NO:6, preferable 99% sequence identity to SEQ ID NO:6.

Leaf and silk bioassays using transgenic maize expressing a truncated version of Cry1Da demonstrated good insect protection against CEW larvae damage. Comparable leaf protection against CEW feeding was observed in both transgenic maize plants expressing truncated Cry1Da and the commercial Herculex® I (HX1) product expressing Cry1Fa.

Surprisingly, protection of CEW larvae feeding of maize silk was found to be superior in transgenic plants expressing truncated Cry1Da as compared to HX1 plants. Insects feeding on silk tissue from transgenic maize expressing truncated Cry1Da experienced mortality (~25%), which was numerically better than observed for insects feeding on silk tissue from HX1 plants (<10%).

CEW is a difficult insect pest to control with *Bacillus thuringiensis* (Bt) proteins, and this is the first described observation where transgenic maize expressing Cry1Da demonstrated biological activity to protect maize silk from feeding damage caused by this insect. Adult CEW moths typically oviposite their eggs on corn silk and the newly emerging larvae feed on corn silk prior to entering the ear. Thus, having insect protectant activity located in maize silk tissues will provide significant protective effects against feeding damage caused by this significant and destructive pest of maize. Deployment options of the subject invention include the use of Cry1Da proteins in geographical regions, including soybean- and corn-growing regions where CEW are present and problematic.

The data presented herein demonstrate that Cry1Da is an excellent protein to control CEW through silk tissues compared to Herculex 1®. As used herein, the terms "control" and "controlling" include growth inhibition and/or mortality.

A Cry1Da/Cry1Ab protoxin chimera is shown herein to have insecticidal activity against *H. zea* in diet insect bioassays. When the truncated form of Cry1Da was expressed in transgenic maize, it protected the plants from leaf and silk feeding damage caused by either CEW or fall armyworm (FAW), *Spodoptera frugiperda*. These results are surprising as Cry1Da was previously reported to not be active against CEW (Karim, 2000) and only active against FAW (Van Frankenhuyzen, 2009). The Cry1Da insecticidal protein is known; however, this invention is a novel and unexpected use of Cry1Da for preventing serious CEW damage to plants, especially crop plants.

*Helicoverpa zea* has a polyphagous larval feeding habit. It feeds preferably on reproductive structures and growing tissues that are nitrogen-rich, such as the maize silk, ear, cob and tassel, cotton boll and bud, as well as soybean pod. It is a very significant insect (pest to crops) because of plant damage directly impacting the crop yield. Apart from maize, Cry1Da has utility to control this insect species in high value crops such as cotton and soybeans, as well as vegetables such as tomatoes.

Insect resistance management (IRM) describes farming practices used to reduce the potential for insect pests to become resistant to a pesticide. IRM is of great importance relative to the use of Cry toxins in major crop plants because insect resistance poses numerous threats to the use Cry toxins in transgenic crops. Specific IRM strategies, such as the high dose and structured refuge have the ability to diminish the likelihood that insects will develop resistance to certain Cry toxins. Effective IRM practices can reduce the risk of resistance development.

On its website, the United States Environmental Protection Agency (epa.gov/oppbppd1/biopesticides/pips/bt_corn_refuge_2006.htm) publishes the following requirements for providing refuges made up of non Cry toxin-bearing plants for use with transgenic crops producing a single Cry toxin active against target pests.

"The specific structured requirements for corn borer-protected Bt (Cry1 Ab or Cry 1F) corn products are as follows:
Structured refuges:
20% non-Lepidopteran Bt corn refuge in Corn Belt;
50% non-Lepidopteran Bt refuge in Cotton Belt
Blocks
Internal (i.e., within the Bt field)
External (i.e., separate fields within ½ mile (½ mile if possible) of the Bt field to maximize random mating)
In-field Strips
Strips must be at least 4 rows wide (preferably 6 rows) to reduce the effects of larval movement"

In addition, the National Corn Growers Association, on its website: (ncga.com/insect-resistance-management-fact-sheet-bt-corn) also provides similar guidance regarding the refuge requirements. For example:

"Requirements of the Corn Borer IRM:
Plant at least 20% of your corn acres to refuge hybrids
In cotton producing regions, refuge must be 50%
Must be planted within ½ mile of the refuge hybrids
Refuge can be planted as strips within the Bt field; the refuge strips must be at least
4 rows wide
Refuge may be treated with conventional pesticides only if economic thresholds are reached for target insect
Bt-based sprayable insecticides cannot be used on the refuge corn
Appropriate refuge must be planted on every farm with Bt corn"

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

Insect Toxins, and Insect Active Variants

In addition to the specifically exemplified genes and proteins as discussed herein, included are insecticidally active variants. By the term "variant", applicants intend to include fragments, certain deletion and insertion mutants, and certain fusion proteins. The Cry1Da protein is a classic three-domain Cry toxin. As a preface to describing variants of the Cry1Da insect toxin that are included in the invention, it will be useful to briefly review the architecture of three-domain Cry toxins in general and of the Cry1Da insect toxin.

A majority of *Bacillus thuringiensis* delta-endotoxin crystal protein molecules are composed of two functional segments. The protease-resistant core toxin is the first segment and corresponds to about the first half of the protein molecule. The full~130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., (1989). The protoxin segment may thus convey a partial insect specificity for the toxin by limiting the accessibility of the core to the insect by reducing the protease processing of the toxin molecule (Haider et al., 1986) or by reducing toxin solubility (Aronson et al., 1991). B.t. toxins, even within a certain class, vary to some extent in length and in the precise location of the transition from the core toxin portion to protoxin portion. The transition from core toxin portion to protoxin portion will typically occur at between about 50% to about 60% of the full length toxin.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains (reviewed in de Maagd et al., 2003).

Insect Toxin Variants Created by Making a Limited Number of Amino Acid Deletions, Substitutions, or Additions Amino acid deletions, substitutions, and additions to the exemplified amino acid sequences can readily be made in a sequential manner and the effects of such variations on insecticidal activity can be tested by bioassay. Provided the number of changes is limited in number, such testing does not involve unreasonable experimentation. The invention includes insecticidally active variants of the core toxin in which up to 10, up to 15, or up to 20 amino acid additions, deletions, or substitutions have been made.

Included are Cry1Da insecticidally active variants that are, including those having a core toxin segment that is, at least 95%, 96%, 97%, 98%, or 99% identical to an exemplified amino acid sequence as used herein. Also included are similar active proteins having at least 90%, 91%, 92%, 93%, or 94% identity with an exemplified sequence.

According to official nomenclature procedures, Cry and B.t. nomenclature is based on boundaries of approximately 95% (Cry1Da's, for example), 78% (Cry1D's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. The following lists of examples of amino acids belonging to each class.

| Class of Amino Acid | Examples of Amino Acids |
|---|---|
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See e.g. U.S. Pat. No. 7,058,515; Larson et al., (2002); Stemmer (1994a, 1994b, 1995); and Crameri et al., (1996a, 1996b, 1997).

Nucleic Acids

Isolated nucleic acids encoding Cry1Da insect toxins are one aspect of the present invention. This includes the subject novel uses of nucleic acids encoding SEQ ID NO:2, SEQ ID NO:4, and SEQ ID NO:6, and complements thereof, as well as other nucleic acids that encode insecticidally active variants. By "isolated" applicants mean that the nucleic acid molecules have been removed from their native environment and have been placed in a different environment by the hand of man. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Coding sequences of the subject invention can be operably linked to a heterologous promoter, including a non-B.t. promoter. Such sequences can be included in expression constructs, transformation cassettes, and expression cassettes including those as present reproducibly in a plant genome, for example.

Gene Synthesis

Genes encoding the improved Cry proteins described herein can be made by a variety of methods well-known in the art. For example, synthetic gene segments and synthetic genes can be made by phosphite tri-ester and phosphoramidite chemistry (Caruthers et al, 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding Cry1Da insect toxins can be made for example, by synthetic construction by methods currently practiced by any of several commercial suppliers. (See for example, U.S. Pat. No. 7,482,119 B2). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a Cry1Da insect toxin, a coding sequence can be designed by reverse translating the amino acid sequence using codons preferred by the intended host, and then refining the sequence using alternative codons to remove sequences that might cause problems and provide periodic stop codons to eliminate long open coding sequences in the non-coding reading frames.

Quantifying Sequence Identity

To determine the percent identity of two amino acid sequences or of two nucleic acid sequences, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST Altschul et al., (1997) can be utilized to obtain gapped alignments for comparison purposes, Alternatively, PSI-Blast can be used to perform an iterated search that detects distant relationships between molecules Altschul et al., (1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., (1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at http://emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (http://emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna. cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts

The insect toxin-encoding genes of the subject invention can be introduced into a wide variety of microbial or plant hosts. Expression of the insect toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the insect toxin gene can be treated under conditions that prolong the activity of the toxin and stabilize the cell. The treated cell, which retains the toxic activity, then can be applied to the environment of the target pest. Non-regenerable/non-totipotent plant cells from a plant of the subject invention (comprising at least one of the subject Cry toxin genes) are included within the subject invention.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g. genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

Methods of Controlling Insect Pests.

When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants.

The subject proteins can be used to protect practically any type of plant from damage by an insect pest. Examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 and 5,141,131). Plants may be transformed using *Agrobacterium* technology, see U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and 5,159,135. Other transformation technology includes WHISKERS™ technology, see U.S. Pat. NoS. 5,302,523 and 5,464,765. Electroporation technology has also been used to transform plants, see WO 87/06614, U.S. Pat. Nos. 5,472,869, 5,384,253, WO 9209696, and WO 9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Genes encoding Cry1Da insecticidal toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent Application No. 120516; Lee and Gelvin (2008), Fraley et al., (1986), and An et al., (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alia. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus, and the like may be used. Plant promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g. other insect resistance conferred by B.t.-derived or other insecticidal proteins, insect resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLE 1

Construction of Plasmids Encoding DIG-911 and DIG-180, and Expression in Bacterial Hosts DIG-911 protein (Cry1Da2/Cry1Ab chimeric insecticidal toxin; SEQ ID NO:2) consists of a core toxin segment of Cry1Da (amino acids 1 to 594, as disclosed in GENBANK Accession No. I76415.1 and U.S. Pat. No. 5,691,308) and a protoxin segment derived from Cry1Ab (DIG-911 amino acids 595 to 1139), essentially as disclosed in GENBANK Accession No. AFK79795.1). The use of the Cry1Da core toxin segment in combinations with other Cry or Vip insecticidal toxins has been previously disclosed in U.S. Patent Application Publication Nos. 20130007923, 20120331590, 20120331589, and 20120317681, but the use of Cry1Da insecticidal protein to control Corn Earworm (CEW; *Helicoverpa zea* (Boddie)) is not contemplated.

Unless otherwise indicated, molecular biological and biochemical manipulations described in this and subsequent EXAMPLES were performed by standard methodologies as disclosed in, for example, Sambrook et al., eds. (1989 and updates, *Molecular Cloning: A Laboratory Manual*, $2^{nd}$ ed.; Cold Spring Harbor Laboratory Press, Plainview, N.Y.), Ausubel et al., eds. (1995 and updates, *Current Protocols in Molecular Biology*. Greene Publishing and Wiley-Interscience, New York) and Harlow & Lane, eds. (1988, and updates, *Antibodies: A Laboratory Manual*. Cold Spring Harbor Laboratories, Cold Spring Harbor, N.Y.). Standard cloning methods were used in the construction of *Pseudomonas fluorescens* (Pf) expression plasmids engineered to produce DIG-911 and DIG-180 (i.e. Cry1Fa2; SEQ ID NO:4) proteins. Plasmid preparations were performed using the NUCLEOSPIN PLASMID KIT (MACHEREY-NAGEL Inc, Bethlehem, Pa.), following the low-copy plasmid isolation instructions of the supplier.

The basic cloning strategy entailed subcloning a DNA fragment having the DIG-911 or DIG-180 coding sequence (CDS), as provided by SEQ ID NO:1 and SEQ ID NO:3, respectively, into pDOW1169 at SpeI or XbaI, and XhoI or SalI restriction sites, whereby the DIG-911 and DIG-180 CDS was placed under the expression control of the Ptac promoter and the rrnBT1T2 terminator from plasmid pKK223-3 (PL PHARMACIA, Milwaukee, Wis.). pDOW1169 is a medium copy plasmid with the RSF1010 origin of replication and a pyrF gene (U.S. Pat. No. 7,618, 799). DNA fragments comprising protein coding region sequences may be cloned into pDOW1169 DNA at a restriction site downstream of a ribosome binding site present within the pDOW1169 sequence, or, alternatively, a separate ribosome binding site may be introduced as a sequence present on the coding region fragment upstream of the protein coding region. DNA of the expression plasmid pDOW2848 (DIG-911) was transformed by electroporation into DC454 cells (a near wild-type *P. fluorescens* strain having mutations ΔpyrF and lsc::lacIQI), and pDAB1817 DNA (DIG-180) was transformed into MB214 cells). Transformed cells were allowed to recover in SOC-Soy hydrolysate medium, and then plated on selective media (M9 glucose agar lacking uracil or on LB medium containing tetracycline at appropriate concentrations; Sambrook et al., supra). Details of the microbiological manipulations for *P. fluorescens* are available in Squires et al. (2004), U.S. Pat. Nos. 7,985,564, 7,681,799, and U.S. Patent Application No. 20080058262, incorporated herein by reference. Recombinant colonies were identified by restriction digestion of miniprep plasmid DNA.

Growth and expression analysis in shake flasks. Production of DIG-911 and DIG-180 proteins for characterization and insect bioassay was accomplished by shake-flask-grown *P. fluorescens* strain DPf150 (harboring plasmid pDOW2848) or strain Dpf129 (harboring plasmid pDAB1817). Seed cultures grown in M9 medium supplemented with 1% glucose and trace elements were used to inoculate 50 mL of defined minimal medium with 5% glycerol (TEKNOVA Cat. #3D7426, Hollister, Calif.). Expression of the DIG-911 or DIG-180 genes via the Ptac promoter was induced by addition of isopropyl-β-D-1-thiogalactopyranoside (IPTG) after an initial incubation of 24 hours at 30° with shaking. Cultures were sampled at the time of induction and at various times post-induction. Cell density was measured by optical density at 600 nm ($OD_{600}$).

Other culture media suitable for growth of *Pseudomonas fluorescens* may also be utilized, for example, as described in Huang et al. (2007, Prot Cell Fractionation and SDS-PAGE Analysis of Shake Flask Samples.

At each sampling time 2 mL aliquots were centrifuged at 14000×g for five minutes, and the cell pellets were stored at −80°. For protein extraction, the pellets were thawed and suspended in 0.5 mL of phosphate buffer pH7.2. Cells were lysed by sonication using a BRANSON 250 SONIFIER (BRANSON ULTRASONICS, Danbury Conn.) using a ⅛ inch diameter micro tip with a constant output of 20 units. Two 45 second bursts were used with several minutes of cooling the sample on ice between bursts. After the lysate was fractionated by centrifugation in a microfuge for 5 minutes at 14,000 rpm, the supernatant (soluble fraction) was removed and the pellet was suspended in 0.5 ml of phosphate buffer (insoluble fraction).

Samples were mixed 1:3 with 4× Laemmli sample buffer containing [3-mercaptoethanol (Sambrook et al., supra) and boiled for 5 minutes prior to loading onto a NOVEX® 4-20% Tris Glycine SDS polyacrylamide gel (INVITROGEN, Carlsbad, Calif.). Electrophoresis was performed in Tris Glycine NOVEX® running buffer (INVITROGEN). Gels were stained with BIO-SAFE Coomassie Stain according to the manufacturer's (BIO-RAD Inc., Hercules, Calif.) protocol.

Inclusion Body Preparation.

Cry protein inclusion body (TB) preparations were performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (P8465 SIGMA-ALDRICH, St. Louis, Mo.) were added just prior to use. Thorough suspension was obtained using a hand-held homogenizer at lowest setting (TISSUE TEAROR™, BIOSPEC PRODUCTS, Inc., Bartlesville, Okla.). Lysozyme (25 mg of SIGMA L7651, from chicken egg white) was added to the cell suspension by mixing with a metal spatula, and the suspension was incubated at room temperature for one hour. The suspension was cooled on ice for 15 minutes, then sonicated using a BRANSON 250 SONIFIER (two 1-minute sessions, at 50% duty cycle, 30% output). Cell lysis was checked by microscopy. An additional 25 mg of lysozyme were added if necessary, and the incubation and sonication were repeated. When cell lysis was confirmed via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile- Solubilization of Inclusion Bodies.

Six mL of inclusion body suspensions from Pf isolates DPf150 or Dpf129 (containing about 30 mg/mL of DIG-911 or DIG-180 protein) were centrifuged on the highest setting of a microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an AMICON ULTRA-15 regenerated cellulose centrifugal filter device (30,000 Molecular Weight Cutoff; MILLIPORE). The sample buffer was then changed to 10 mM CAPS (3-(cyclohexamino)-1-propanesulfonic acid) pH10, using disposable PD-10 columns (GE HEALTHCARE, Piscataway, N.J.).

SDS-PAGE analysis and quantitation of protein in IB preparations were done by thawing a 1 mL aliquot of IB pellet and diluting 1:20 with sterile-filtered distilled water. The diluted sample was then boiled with 4× reducing sample buffer (250 mM Tris, pH6.8, 40% glycerol (v/v), 0.4% Bromophenol Blue (w/v), 8% SDS (w/v) and 8% β-Mercapto-ethanol (v/v)) and loaded onto a NOVEX® 4-20% Tris-Glycine, 12+2 well gel (INVITROGEN) run with 1× Tris/Glycine/SDS buffer (BIO-RAD). The gel was run for approximately 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve. The concentrated extract was prepared for electrophoresis by diluting 1:50 in NuPAGE® LDS sample buffer (INVITROGEN) containing 5 mM dithiothreitol as a reducing agent and heated at 95° for 4 minutes. The sample was loaded in duplicate lanes of a 4-12% NuPAGE® gel alongside five BSA standards ranging from 0.2 to 2 µg/lane (for standard curve generation). Voltage was applied at 200V using MOPS SDS running buffer (INVITROGEN) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a BIO-RAD FLUOR-S MULTIIMAGER. The instrument's QUANTITY ONE v.4.5.2 Software was used to obtain background-subtracted volumes of the stained protein bands and to generate the BSA standard curve that was used to calculate the concentration of DIG-911 or DIG-180 protein in the stock solution.

EXAMPLE 2

Activity of DIG-911 and DIG-180 Insecticidal Toxins Produced in *Pseudomonas fluorescens* Against CEW Larvae Sample Preparation and Bioassays.

Inclusion body preparations in 10 mM CAPS pH 10 were diluted in the same buffer to deliver a dose of 3,000, 1,000, 333.3, 111.1, 37.0, 12.3 or 4.1 ng/cm$^2$ of the target Cry1Da protein. All bioassays contained control treatments consisting of 10 mM CAPS pH 10 buffer or water, which served as background checks for mortality or growth inhibition.

Protein concentrations in bioassay buffer were estimated by gel electrophoresis using BSA to create a standard curve for gel densitometry, which was measured using a BIORAD imaging system (FLUOR-S MULTIIMAGER with QUANTITY ONE software version 4.5.2). Proteins in the gel matrix were stained with Coomassie Blue-based stain and destained before reading.

Larvae of CEW were hatched from eggs obtained from a colony maintained by a commercial insectary (BENZON RESEARCH INC., Carlisle, Pa.). The bioassays were conducted in 128-well plastic trays specifically designed for insect bioassays (C-D INTERNATIONAL, Pitman, N.J.). Each well contained 1.5 mL of Multi-species Lepidoptera diet (SOUTHLAND PRODUCTS, Lake Village, Ark.). A 40 μL aliquot of protein sample was delivered by pipette onto the 1.5 cm$^2$ diet surface of each well (26.7 μL/cm$^2$). Diet concentrations were calculated as the amount (ng) of insecticidal toxin protein per square centimeter (cm$^2$) of surface area in the well. The treated trays were held in a fume hood until the liquid on the diet surface had evaporated or was absorbed into the diet.

Within 24 to 48 hours of eclosion, individual larvae were picked up with a moistened camel hair brush and deposited on the treated diet, one larva per well. The infested wells were then sealed with adhesive sheets of clear plastic, vented to allow gas exchange (C-D INTERNATIONAL). Bioassay trays were held under controlled environmental conditions (28°, ~60% Relative Humidity, 16:8 (Light:Dark)) for 5 days, after which time the total number of insects exposed to each protein sample, the number of live and dead insects, and the weight of surviving insects were recorded. Percent mortality and percent growth inhibition were calculated for each treatment. Growth inhibition (GI) was calculated as follows:

$$GI=[1-(TWIT/TNIT)/(TWIBC/TNIBC)]$$

where TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

The mortality and growth inhibition data were analyzed by a nominal logistic regression ($P<0.05$). The $GI_{50}$ was determined to be the concentration of insecticidal toxin protein in the diet at which the GI value was 50%, and the LC50 (50% Lethal Concentration) was recorded as the concentration of insecticidal toxin protein in the diet at which 50% of test insects were killed. Statistical analysis (One-way ANOVA) was done using JMP® Pro software (version 9.0.3; SAS, Cary, N.C.). Table 1 shows the activities of DIG-911 and DIG-180 proteins as measured in diet bioassays

TABLE 1

Activities of DIG-911 And Cry1Fa proteins in diet bioassays against neonate larvae of corn earworm (CEW).

| | | Mortality | | Growth Inhibition | |
|---|---|---|---|---|---|
| Insect | Protein | $LC_{50}$ (ng/cm$^2$) | 95% CI* | $GI_{50}$ (ng/cm$^2$) | 95% CI |
| CEW | DIG-911 | 2193 | (1551-3351) | 75 | (49-116) |
| | Cry1Fa2 | 10771 | (6158-23007) | 94 | (45-195) |

*= Confidence Interval

The data of Table 1 document the surprising discovery that the DIG-911 protein, comprising the Cry1Da core toxin segment, exhibits both mortality and growth inhibition activity against corn earworm (CEW) larvae. This result is in contrast to results reported by others that the Cry1Da protein is inactive against corn earworm (See Karim et al. (2000) Pesticide Biochemistry and Physiology 67(3): 198-216; and Frankenhuyzen (2009) Journal of Invertebrate Pathology. 101:1-16).

EXAMPLE 3

Construction of Plant Transformation Vectors

Gateway® (INVITROGEN) entry vectors were constructed by standard molecular cloning methods. Entry vector pDAB 109825 comprises a maize-optimized coding sequence (SEQ ID NO:5) that encodes a Cry1Da2 core toxin insecticidal protein (SEQ ID NO:6). Entry vector pDAB 109840 comprises a maize-optimized coding sequence that encodes a Cry1Da2 full length insecticidal protein. Plant expression of the Cry1Da2 core toxin coding sequence is under the control of a copy of a maize ubiquitin 1 promoter with associated intron 1 (U.S. Pat. No. 5,510,474). A fragment comprising a 3'UTR from a maize peroxidase 5 gene (ZmPer5 3'UTR; U.S. Pat. No. 6,699,984) was used to terminate transcription of the Cry1Da2 mRNA. A transformation/expression vector (pDAB109841) for *Agrobacterium*-mediated maize embryo transformation was constructed through the use of standard cloning methods and Gateway® recombination reactions employing a typical destination binary vector (pDAB 109805) and entry vector pDAB 109825 described above. Binary destination vector pDAB 109805 comprises an AAD-1 herbicide tolerance protein coding region (U.S. Pat. No. 7,838,733, and Wright et al. (2010) Proc. Natl. Acad. Sci. U.S.A. 107:20240-20245) under the expression control of a copy of a sugarcane bacilliform virus promoter (SCBV; essentially as described in U.S. Pat. No. 6,093,569). A synthetic 5'UTR sequence comprised of sequences from a Maize Streak Virus (MSV) coat protein gene 5'UTR and intron 6 from a maize Alcohol Dehydrogenase 1 (ADH1) gene is positioned between the 3' end of the SCBV promoter segment and the start codon of the AAD-1 coding region. A fragment comprising a 3'UTR from a maize lipase gene (as above) was used to terminate transcription of the AAD-1 mRNA.

A negative control binary vector (pDAB101556) comprised a yellow fluorescent protein (YFP) marker gene coding region (Shagin et al. (2004) Molecular Biology and Evolution 21:841-850) under the expression control of a copy of a maize ubiquitin 1 promoter with intron1 (as above) and a fragment comprising a 3'UTR from a maize peroxidase 5 gene (ZmPer5 3'UTR; U.S. Pat. No. 6,699,984). pDAB101556 further comprises an AAD-1 herbicide tolerance protein coding region (as above) under the expression control of a second copy of a maize ubiquitin 1 promoter with intron1 (as above), and a 3'UTR from a maize lipase gene (as above).

EXAMPLE 4

*Agrobacterium*-Mediated Maize Transformation

*Agrobacterium*-mediated transformation was used to stably integrate a Cry1Da2 core toxin coding region into the plant genome and thus generate transgenic maize cells, tissues, and plants that produce a full length or truncated Cry1Da2 insecticidal protein. Maize transformation methods employing superbinary or binary transformation vectors are known in the art, as described, for example, in International PCT Publication No. WO2010/120452. Transformed tissues were selected by their ability to grow on R-Haloxyfop-containing medium.

*Agrobacterium* Culture Initiation

Glycerol stocks of the project vectors were provided in the *Agrobacterium tumefaciens* host strain DAt13192 (WO 2012/016222A2). *Agrobacterium* cultures were streaked from glycerol stocks onto AB minimal medium (Watson, et al., (1975) J. Bacteriology 123:255-264) and incubated at 20° C. in the dark for 3 days containing appropriate antibiotics. The cultures were then streaked onto a plate of YEP medium (gm/L: yeast extract, 10; Peptone, 10; NaCl, 5) with antibiotics and incubated at 20° C. in the dark for 1-3 day.

On the day of an experiment, a mixture of Inoculation Medium and acetosyringone (Frame et al. (2011) Methods in Molecular Biology 710:327-341) was prepared in a volume appropriate to the number of constructs in the experiment and pipetted into a sterile, disposable, 250 mL flask. Inoculation Medium contains: 2.2 gm/L MS salts; Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone was added to the flask containing Inoculation Medium to a final concentration of 200 µM from a 1 M stock solution in 100% dimethyl sulfoxide.

For each construct, 1 inoculating loopful of *Agrobacterium* from the YEP plate was suspended in 15 mL of the Inoculation Medium/acetosyringone mixture inside a sterile, disposable, 50 mL centrifuge tube, and the optical density of the solution at 550 nm ($OD_{550}$) was measured in a spectrophotometer. The suspension was then diluted to $OD_{550}$ of 0.3 to 0.4 using additional Inoculation Medium/acetosyringone mixture. The tube of *Agrobacterium* suspension was then placed horizontally on a platform shaker set at about 75 rpm at room temperature and shaken for 1 to 4 hours before use.

Ear Sterilization and Embryo Isolation.

Ears from *Zea mays* inbred line B104 (Hallauer, et al. (1997) Crop Science 37:1405-1406) were produced in a greenhouse and harvested 10 to 12 days post pollination. Harvested ears were de-husked and surface-sterilized by immersion in a 20% solution of commercial bleach (Ultra Clorox® Germicidal Bleach, 6.15% sodium hypochlorite; with two drops of TWEEN 20) for 20 minutes, followed by three rinses in sterile, deionized water inside a laminar flow hood. Immature zygotic embryos (1.8 to 2.2 mm long) were aseptically excised from each ear and distributed into one or more micro-centrifuge tubes containing 2.0 mL of *Agrobacterium* suspension into which 2 µL of 10% BREAK-THRU® S233 surfactant (EVONIK INDUSTRIES; Essen, Germany) had been added.

*Agrobacterium* Co-Cultivation.

Following isolation, the embryos were placed on a rocker platform for 5 minutes. The contents of the tube were then poured onto a plate of Co-cultivation Medium, which contains 4.33 gm/L MS salts; Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 200 µM acetosyringone in DMSO; and 3 gm/L agar (SIGMA-ALDRICH, plant cell culture tested) at pH 5.8. The liquid *Agrobacterium* suspension was removed with a sterile, disposable, transfer pipette and co-cultivation plate containing the embryos was placed at the back of the laminar flow hood with the lid ajar for 30 minutes, after which time the embryos were oriented with the scutellum facing up using sterile forceps with the aid of a microscope. The plate was returned to the back of the laminar flow hood with the lid ajar for a further 15 min.

The plate was then closed, sealed with 3M™ Micropore™ medical tape, and placed in an incubator at 25° C. with continuous light at approximately 60 µEm$^{-2}$ sec$^{-1}$ light intensity Callus Selection and Regeneration of Transgenic Events.

Following the co-cultivation period, embryos were transferred to Resting Medium, which is composed of 4.33 gm/L MS salts; Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L AgNO$_3$; 0.5 gm/L MES (2-(N-morpholino)ethanesulfonic acid monohydrate; Phytotechnologies labr.; Lenexa, Kans.); 250 mg/L Cefotaxime; and 7.0 gm/L agar; at pH 5.8. No more than 36 embryos were moved to each plate. The plates were wrapped with Micropore™ tape and incubated at 27° C. with continuous light at approximately 50 µEm$^{-2}$ sec$^{-1}$ light intensity for 7 to 10 days. Embryos with callus (<18/plate) were then transferred onto Selection Medium I, which is comprised of Resting Medium (above) but with only 6.5 gm/L agar, and with 100 nM R-Haloxyfop acid (0.0362 mg/L. The plates were wrapped with Micropore™ tape and incubated at 27° C. with continuous light at approximately 50 µEm$^{-2}$ sec$^{-1}$ light intensity for 7 days. Proliferated Callus (<12/plate) were then transferred to Selection Medium II, which is comprised of Resting Medium (above) but with only 6.5 gm/L agar, and with 500 nM R-Haloxyfop acid (0.181 mg/L). The plates were wrapped and incubated at 27° C. with continuous light at approximately 50 µEm$^{-2}$ sec$^{-1}$ light intensity for 14 days.

At this stage, resistant calli (<9/plate) were moved to Pre-Regeneration medium. Pre-Regeneration Medium contains 4.33 gm/L MS salts; Modified MS Vitamins; 45 gm/L sucrose; 350 mg/L L-proline; 100 mg/L myo-inositol; 50 mg/L Casein Enzymatic Hydrolysate; 1.0 mg/L AgNO$_3$; 0.5 gm/L MES; 0.5 mg/L naphthaleneacetic acid in NaOH; 2.5 mg/L abscisic acid in ethanol; 1 mg/L 6-benzylaminopurine; 250 mg/L Cefotaxime; 5.5 gm/L agar; and 500 nM R-Haloxyfop acid (0.181 mg/L), at pH 5.8. The plates were wrapped and incubated at 27° C. with continuous light at approximately 50 µEm$^{-2}$ sec$^{-1}$ light intensity for 7 days. Regenerating calli (<6/plate) were then transferred to Regeneration Medium in Phytatrays™ (Sigma-Aldrich) and incubated at 28° C. with 16 hours light/8 hours dark per day at approximately 150 µmol m$^{-2}$ s$^{-1}$ light intensity for 14 days or until shoots developed. Regeneration Medium contains 4.33 gm/L MS salts; Modified MS Vitamins; 60 gm/L sucrose; 0.50 gm/L MES; 125 mg/L Cefotaxime; 5.5 gm/L agar; and 500 nM R-Haloxyfop acid (0.181 mg/L), at pH 5.8. Small shoots with primary roots were then isolated and transferred to Elongation Medium without selection (i.e. Regeneration Medium without R-Haloxyfop acid and with 30 gm/L sucrose instead of 60 gm/L sucrose) for further growth. Rooted plantlets about 6 cm or taller were transplanted into soil and moved to a growth chamber for hardening off.

Transfer and Establishment of $T_0$ Plants in the Greenhouse for Assay and Seed Production.

Transformed plant tissues selected by their ability to grow on medium containing Haloxyfop were transplanted from Phytatrays™ to small pots (T. O. Plastics, 3.5" SVD) filled with growing media (PROMIX BX; Premier Tech Horticulture), covered with humidomes (Arco Plastics Ltd.), and then hardened-off in a growth room (28° C. day/24° C. night, 16-hour photoperiod, 50-70% RH, 200 µEm$^{-2}$ sec$^{-1}$ light intensity). When plants reached the V3-V4 stage, they were transplanted into Sunshine Custom Blend 160 soil mixture and grown to flowering in the greenhouse (Light Exposure Type: Photo or Assimilation; High Light Limit: 1200 PAR; 16-hour day length; 27° C. day/24° C. night). Putative transgenic plantlets were analyzed for transgene copy number by quantitative real-time PCR assays using primers designed to detect relative copy numbers of the transgenes, and events having only one or two copies of the integrated Cry1Da2 gene were transplanted into 5 gallon pots. Observations were taken periodically to track any abnormal phenotypes. Plants of the $T_1$ generation were obtained by self-pollinating the silks of $T_0$ transgenic plants with pollen collected from the $T_0$ plants and planting the resultant seeds. $T_1$ seeds from event 109841 [3]-106 were planted and selected by spraying the plants with Quizalofop, and keeping the surviving plants until the reproduction stage to obtain silks for corn earworm bioassays and western blot analyses.

Transgenic maize plants were similarly produced following transformation with binary vector pDAB 101556 harboring a yellow fluorescent protein gene expression cassette.

EXAMPLE 5

Molecular and Biochemical Analyses of Transgenic Maize Tissues

Hydrolysis Probe qPCR for copy number analysis. Molecular analyses were employed to screen for low copy, simple events. Leaf tissue was collected from rooted putative transgenic plants before transplanting to soil. DNA was extracted with a QIAGEN MagAttract™ kit using the Biosprint96, QIAGEN extraction robot and the supplier's recommended protocols. Integrated transgene copy number analysis was performed using specific Hydrolysis Probe assays for the AAD-1 gene. In addition, contamination by inadvertent integration of the binary vector plasmid backbone was detected by a Hydrolysis Probe assay specific for the Spectinomycin (Spec) resistance gene borne on the binary vector backbone. Hydrolysis Probe assay for endogenous maize genes Invertase; (GenBank™ Accession No. U16123) was developed as internal reference standard. Table 2 lists the oligonucleotide sequences of the Hydrolysis Probe assay components (synthesized by Integrated DNA Technologies, Coralville, Iowa & Applied Biosystems, Foster City, Calif.). Biplex Hydrolysis Probe PCR reactions were set up according to Table 3 with about 10 ng of DNA, and assay conditions are presented in Table 4.

TABLE 2

List of forward and reverse nucleotide primers and fluorescent probes used for transgene copy number and relative expression detection.

| Gene Detected | Oligo-nucleotide ID* | SEQ ID NO: | Sequence |
|---|---|---|---|
| AAD-1 | AAD1F | 7 | TGTTCGGTTCCCTCTACCAA |
|  | AAD1R | 8 | CAACATCCATCACCTTGACTGA |
|  | AAD1P *(FAM Probe) | 9 | CACAGAACCGTCGCTTCAGCAACA |
| Spec | SPC1A | 10 | CTTAGCTGGATAACGCCAC |
|  | SPC1S | 11 | GACCGTAAGGCTTGATGAA |
|  | TQSPC (FAM Probe) | 12 | CGAGATTCTCCGCGCTGTAGA |

TABLE 2-continued

List of forward and reverse nucleotide primers and fluorescent probes used for transgene copy number and relative expression detection.

| Gene Detected | Oligo-nucleotide ID* | SEQ ID NO: Sequence |
|---|---|---|
| Maize Invertase | InvertaseF | 13 TGGCGGACGACGACTTGT |
| | InvertaseR | 14 AAAGTTTGGAGGCTGCCGT |
| | InvertaseP (HEX Probe) | 15 CGAGCAGACCGCCGTGTACTT |

*Fluorescent probe labels are: FAM = 6-Carboxy Fluorescein Amidite; HEX = hexachloro-fluorescein; MGB & VIC = "Minor Groove Binder"; VIC ® is a proprietary fluorescent label from INVITROGEN.

TABLE 3

Hydrolysis Probe PCR mixture for transgene DNA copy number analysis.

| Reaction Component | μL | Final Concentration |
|---|---|---|
| Water | 0.6 | |
| ROCHE 2X Master Mix | 5 | 1X |
| Transgene Forward Primer (10 μM) | 0.4 | 0.4 μM |
| Transgene Reverse Primer (10 μM) | 0.4 | 0.4 μM |
| Transgene Probe (5 μM) | 0.4 | 0.2 μM |
| Invertase Forward Primer (10 μM) | 0.4 | 0.4 μM |
| Invertase Reverse Primer (10 μM) | 0.4 | 0.4 μM |
| Invertase Probe (5 μM) | 0.4 | 0.2 μM |

TABLE 4

Thermocycler conditions for Hydrolysis Probe PCR amplification

| PCR Steps | Temp (° C.) | Time | No. of cycles |
|---|---|---|---|
| Denature/Activation | 95 | 10 min | 1 |
| Denature | 95 | 10 sec | 40 |
| Anneal/Extend | 60 | 40 sec | |
| Acquire | 72 | 1 sec | |
| Cool | 40 | 10 sec | 1 |

For amplification, LIGHTCYCLER®480 Probes Master mix (Roche Applied Science, Indianapolis, Ind.) was prepared at 1× final concentration in a 10 μL volume multiplex reaction, 0.4 μM of each primer, and 0.2 μM of each probe. The FAM (6-Carboxy Fluorescein Amidite) fluorescent moiety was excited at 465 nm and fluorescence was measured at 510 nm; the corresponding value for the HEX (hexachlorofluorescein) fluorescent moiety were 533 nm and 580 nm. The level of fluorescence generated for each reaction was analyzed using the Roche Lightcycler®480 Real-Time PCR system according to the manufacturer's recommendations. Transgene copy number was determined by comparison of Lightcycler®480 outputs of Target/Reference gene values for unknown samples to Target/Reference gene values of known copy number standards (1-Copy representing hemizygous plants, 2-Copy representing homozygous plants).

Cp scores, i.e., the point at which the florescence signal crosses the background threshold using the fit points algorithm (Lightcycler® software release 1.5), and the Relative Quant module, were used to perform the analysis of real time PCR data.

In the Lightcycler® Fit Points Algorithm software, a graph of the data is made by plotting the logarithm of the input DNA template concentration against the measured Cp values. The slope of the curve is a desired comparison parameter; therefore the initial log input number can be an arbitrary starting point on the curve, with the caveat that the arbitrary concentration values used for input DNA template are representative of the actual serial dilution used. For example, for a 10-fold serial dilution series, the actual inputs concentrations may be 1000, 100, 10 etc., for which points the LC480 Fit Points Algorithm software plots 3, 2, 1 etc. as the logarithms of the inputs. Using a linear regression, the resulting best fit of this line (input log vs Cp) is then used to estimate a slope (m) from an equation of the form y=mx+b. There is an inverse relationship between the starting template amount and Cp value, and therefore the slope (m) is always negative.

A perfect (i.e. 100% efficient) PCR reaction doubles the total template every cycle. PCR efficiency (Eff) is calculated as: Eff=10e(−1/m). Thus, the slope (m) of the graph of log input vs Cp will be −3.3219 for a perfectly efficient reaction (whose efficiency is defined as 2.00).

In other words, a 100% efficient PCR reaction is defined by: 2.0=10e(−1/−3.3219) The LC480 Fit Points Algorithm software reports the efficiency value by the first formula. So a 99% efficient reaction has an Eff value of 1.99 rather than 0.99. To express this as a percent efficiency, subtract 1 from this value and multiply by 100. Or, % Eff=[(10e(−1/m)−1)]×100

Detection of Plant-Produced Truncated Cry1Da2 Protein.

Proteins were extracted from 200 to 240 mg of ear silks (collected from unpollinated ears) in 0.6 mL of PBST (PBS buffer containing 0.05% Tween 20). A 2 mm steel bead was added, the tubes were capped and secured in a GENO/GRINDER (CERTIPREP; Metuchen, N.J.), and shaken for 5 min at 1500 rpm. Tubes were centrifuged at 4000 rpm for 7 min at 4° C., and supernatants containing the soluble proteins were stored at −80° C. until used.

Total protein concentrations were determined using a PIERCE 660 nm PROTEIN ASSAY kit (THERMO SCIENTIFIC; Rockford, Ill.) following the supplier's instructions. Protein immunoblot analyses were conducted using a polyclonal antibody generated in rabbits using standard procedures (See, for example, Harlow, E., and Lane, D. P. (1988) Antibodies: A Laboratory Manual. Cold Springs Harbor Laboratories, Cold Spring Harbor, N.Y., and updates thereof). Samples were prepared and proteins were separated by electrophoresis through NUPAGE 4-12% Bis-Tris gels in MES running buffer according to the manufacturer's suggested protocol for denaturing electrophoresis (INVITROGEN). Proteins were transferred onto nitrocellulose membrane for 80 min, at 30 V in NUPAGE transfer buffer. Blots were blocked for 1 hour at room temperature in 5% milk/PBST (PBS with 0.05% Tween-20) and then probed with primary antibody (specific for Cry1Da core toxin protein) and then secondary antibodies for one hour each at room temperature in blocking solution, with rinsing in between each antibody for 15 minutes in PBST. Development of blots was done using PIERCE's ECL WESTERN blotting substrate according the manufacturer's protocol (THERMO FISHER SCIENTIFIC, Rockford, Ill.). The presence of truncated Cry1Da proteins was confirmed in extracts from duplicate samples of the silk tissues of maize plants generated from event 109841 [3]-106 (plants 109841 [3]-106.AJ001.008, 109841[3]-106.AJ001.013, 109841[3]-106.AJ001.020, 109841[3]-106.AJ001.027, and 109841 [3]-106.AJ001.028). Two bands were typically detected, one at mobility corresponding to approximately 65 kDa, which corresponds to the molecular size of the Cry1Da2 protein encoded by construct pDAB109841, and a second band having a mobility corresponding to proteins somewhat smaller than 65 kDa. The smaller proteins may correspond to the products remaining after cleavage of amino acids 1-28 from the N-terminus of the Cry1Da core toxin protein. (Processing of a few N-terminal amino acids from Cry1 proteins is often detected.) No such bands were seen in silk extracts from non-transgenic B104 plants.

TABLE 5

Analysis of T1 plants for RNA relative transcript level (RTL) and protein expression.

| Background | Description | Total number of events | Events | RNA total RNA RTL | Total plants | Average RTL/event | Western | Protein Total expression fmole/cm$^2$ | Total plants | Average expression fmole/cm$^2$ |
|---|---|---|---|---|---|---|---|---|---|---|
| 109840 | Cry1Da FL | 2 | 109840[1]-254.AJ001 | 3.7 | 5 | 0.7 | positive | 820 | 5 | 164.0 |
|  |  |  | 109840[2] -121.AJ001 | 2.3 | 5 | 0.5 | negative | 356 | 4 | 89.0 |
|  |  |  | background summary | 5.9 | 10 | 0.6 |  | 1176.0 | 9.0 | 130.7 |
|  |  |  | 109841 [1]-183.AJ001 | 2.73 | 5 | 0.5 | positive | 2270 | 5 | 454.0 |
|  |  |  | 109841 [1]-185. AJ001 | 1.99 | 5 | 0.4 | positive | 3220 | 5 | 644.0 |
|  |  |  | 109841 [1]-187.AJ001 | 1.71 | 5 | 0.3 | positive | 2800 | 5 | 560.0 |
|  |  |  | 109841 [1]-188. AJ001 | 1.86 | 5 | 0.4 | negative | 3350 | 5 | 670.0 |
|  |  |  | 109841 [1]-189.AJ 001 | 2.28 | 5 | 0.5 |  | 4000 | 5 | 800.0 |
|  |  |  | 109841 [2]-021. AJ001 | 2.35 | 5 | 0.5 | negative | 2990 | 5 | 598.0 |
|  |  |  | 109841 [3]-106.AJ001 | 1.82 | 5 | 0.4 |  | 3670 | 5 | 734.0 |
|  |  |  | 109841 [3]-108.AJ001 | 2.62 | 5 | 0.5 |  | 4750 | 5 | 950.0 |
|  |  |  | 109841 [3]-116. AJ001 | 3.16 | 5 | 0.6 | positive | 3910 | 5 | 782.0 |
| 109841 | Cry1Da Tr | 9 | background summary | 20.52 | 45 | 0.5 |  | 30960.00 | 45.00 | 688.0 |

* Measurements were conducted by Western analysis and quantified by LC/MS/MS as known in the art.

EXAMPLE 6

Bioassay of Transgenic Maize Tissues

V5 Leaf Bioassays with T$_1$ Maize Events.

Bioassay trays (32-wells/tray; C-D International) were partially filled with a 2% agar solution and the agar was allowed to solidify. Two leaf sections (about one square inch in area) were taken from each plant and each was placed in a separate well of the 32-well trays. Ten neonate *Helicoverpa zea* (CEW) larvae (about 24 to 48 hr after eclosion) were placed into each well. The trays were sealed with perforated sticky lids to allow ventilation during the test and were then placed at 28° C., 40% RH, 16 hours light: 8 hours dark. After three days, a simple percent leaf area damage score was taken for each leaf piece. Damage scores for each test were averaged.

Corn Earworm Silk Bioassays.

Unpollinated ears were collected, their length was measured, and the ears were stored at 4° C. until used for bioassay. About 10 mL of 2% water agar was placed in the bottom each assay well (about 1 inch square) of a 32-well-bioassay tray to supply moisture to the silks and corn earworm larvae. Five strands of silks (about 10 cm long) were fed to two CEW neonates in each well. Each event was tested in four replicates (wells) in a completely randomized format. After insect infestation, trays were sealed with perforated sticky lids to allow ventilation during the test. Trays were placed at 28° C., 60% RH, 16 hours light:8 hours dark. At 3 days after infestation, the percent silk damage was recorded by visual assessment of the amount of feces on the silk tissues. The numbers of alive, dead and missing insects were recorded per event and percent larval mortality was estimated.

Plant-Produced Cry1Da Activity on CEW Larvae.

Immunoblot analyses detected Cry1Da core toxin protein in silks of ears of T$_1$ pDAB109841 transgenic plants, and the silks provided excellent protection against feeding damage by *H. zea* larvae, having only 4.6% silk damage in the bioassays (Table 6). Silks from negative control transgenic maize plants producing the non-insecticidal yellow fluorescent protein (YFP; construct pDAB 101556), or non-transgenic B104 plants, experienced 90% to 95% mean silk damage by *H. zea* larvae. In addition, the mortality of larvae feeding on silk from plants producing the Cry1Da core toxin protein was 26.8%, while no mortality of the larvae was observed on the negative control plant samples. The Cry1Da construct gave excellent leaf protection of the V5 stage samples, with the pDAB109851 transgenic plants having 12% to 25% leaf damage caused by *H. zea* (Table 6), whereas the negative control plants (B104 and YFP-producing) experienced almost 100% leaf damage. The results from both silk and leaf bioassays demonstrated that the Cry1Da core toxin protein is highly effective in protecting maize plants from damage from *H. zea* larvae.

TABLE 6

Results of bioassays with *H. zea* neonate larvae on samples from Cry1Da core toxin-producing plants, as compared to negative control plants. Means within a column were separated by the Tukey-Kramer HSD test.

| Plant ID | Cry1Da Protein immuno-blot | Ear Length (cm) | % CEW Mortality* | Mean % Silk Damage* | Mean Leaf Damage at V5 |
|---|---|---|---|---|---|
| pDAB109841 Events ||||||
| 109841[3]-106.AJ001.008 | + | 11.4 | 0.0 | 5.0 | 25 |
| 109841[3]-106.AJ001.008 | + | 14.2 | 28.6 | 7.5 |  |
| 109841[3]-106.AJ001.013 | + | 13.6 | 0.0 | 5.0 | 16.7 |
| 109841[3]-106.AJ001.013 | + | 14 | 12.5 | 3.8 |  |
| 109841[3]-106.AJ001.020 | + | 11.9 | 50.0 | 2.5 | 20 |

TABLE 6-continued

Results of bioassays with H. zea neonate larvae on samples from Cry1Da
core toxin-producing plants, as compared to negative control plants.
Means within a column were separated by the Tukey-Kramer HSD test.

| Plant ID | Cry1Da Protein immuno-blot | Ear Length (cm) | % CEW Mortality* | Mean % Silk Damage* | Mean Leaf Damage at V5 |
|---|---|---|---|---|---|
| 109841[3]-106.AJ001.020 | + | 16.3 | 50.0 | 5.0 | |
| 109841[3]-106.AJ001.027 | + | 12.5 | 75.0 | 3.8 | 20 |
| 109841[3]-106.AJ001.027 | + | 13.2 | 37.5 | 3.8 | |
| 109841[3]-106.AJ001.028 | + | 13.9 | 14.3 | 5.0 | 11.7 |
| 109841[3]-106.AJ001.028 | + | 11.2 | 0.0 | 5.0 | |
| Overall Averages | NA** | 13.2 | 26.8 (A)*** | 4.6 (B)*** | 18.7 (B)*** |
| Transgenic Negative Controls: pDAB101556 Events | | | | | |
| 101556[3]-004.001AJ.002 | − | 9.9 | 0.0 | 86.3 | 95-100 |
| 101556[3]-004.001AJ.002 | − | 18.5 | 0.0 | 83.8 | |
| 101556[3]-004.001AJ.002 | − | 13.9 | 0.0 | 95.0 | |
| 101556[3]-004.001AJ.007 | − | 15 | 0.0 | 95.0 | |
| 101556[3]-004.001AJ.008 | − | 12.7 | 0.0 | 93.8 | |
| Overall Averages | NA | 14.2 | 0.0 (B) | 90.8 (A) | 95-100 (A) |
| Non-transgenic Negative Controls: B104 Plants | | | | | |
| B104 #46749 | − | 9 | 0.0 | 88.3 | 95-100 |
| B104 #47153 | − | 9.4 | 0.0 | 97.5 | |
| B104 #47153 | − | 12.2 | 0.0 | 96.3 | |
| B104 #47156 | − | 13.7 | 0.0 | 95.0 | |
| B104 #47157 | − | 14.1 | 0.0 | 91.7 | |
| B104 #47869 | − | 12.6 | 0.0 | 97.5 | |
| B104 #47870 | − | 11.4 | 0.0 | 98.8 | |
| Overall Averages | NA | 11.8 | 0.0 (B) | 95.0 (A) | 95-100 (A) |

*Average of 4 replicates
**NA = Not Applicable
***Levels not connected by same letter within a column are significantly different.

Table 7 shows percent mortality, percent leaf damage and percent silk damage of *H. zea*. The amount of silk damage was scored according to visual insect frass amount on the tissues. Percentage leaf damage was scored according to visual assessment of the larval feeding area on 1 inch square leaf cutting. Maize variety B104 and construct 101556 (or construct 109812 for leaf damage) were negative controls from the hybrid cultivar and yellow fluorescent protein (YFP) control respectively, while HX1 was a commercial hybrid Herculex® I, expressing Cry1Fa protein. Construct 109841 was T1 maize expressing the truncated version of the Cry1Da. Data were analyzed by ANOVA and Tukey-Kramer means separation test.

TABLE 7

Percent mortality, percent leaf damage
and percent silk damage of *H. zea*.

| Treatment | % Mortality ± SEM* | % Silk Damage ± SEM* | % Leaf Damage ± SEM* |
|---|---|---|---|
| 109841 | 26.79 ± 5.41 (A) | 4.64 ± 1.9(A) | 16.5 ± 0.59 (A) |
| HX1 | 4.17 ± 9.87 (AB) | 39.2 ± 3.47 (B) | 18.9 ± 2.27 (A) |
| 101556 or 109812** | 0 ± 7.65 (B) | 90.78 ± 2.69 (C) | 97.77 ± 2.27 (B) |
| B104 | 0 ± 6.46 (B) | 95.01 ± 2.27 (C) | 95.53 ± 2.27(B) |

*Sem = Standard Error of the Mean. Letters in parentheses designate statistical levels. Levels not connected by same letter are significantly different (P < 0.05).
**Construct 109812 was the YFP negative control for the leaf damage bioassay.

EXAMPLE 7

Field Efficacy of Cry1Da Core Toxin Protein Against CEW

Seeds from eight $T_1$ pDAB 109841 transgenic B104 events were tested in field test plots at the DOW AGROSCIENCES Field Station, Fowler, Ind. These events had been analyzed by molecular techniques as described above and were found to be single copy events having no detectable binary vector backbone sequences. All of the events were tested as $T_1$ plants segregating 1:1 (hemizygous:null) for the Cry1Da/AAD1 integration event. Negative controls were nontransgenic B104 (Null) plants.

Test plots contained one 20 foot row for each tested insect species. Treatments were planted in a randomized complete block design with four replicates. The experimental entries were treated at the V2 stage with ASSURE® II (DUPONT™ CROP PROTECTION, Wilmington, Del.) at 184 gm acid-equivalents per hectare (ae/ha)+1% COC to eliminate the null plants. ASSURE® II contains active ingredient (ai) Quizalofop P-Ethyl Ethyl(R)-2-4-[4-6-chloroquinoxalin-2-yl oxy)-phenoxy]propionate. The commercial product contains 0.88 lb ai per gallon and 1.0% (v/v) crop oil concentrate (COC). COC is an emulsifiable refined paraffinic oil containing about 85% paraffinic oil and about 15% emulsifiers. Stand counts were taken 2 weeks after treatment. Five plants per plot were evaluated for insect damage.

Corn earworm eggs (CEW; *Helicoverpa zea* Boddie) were supplied by BENZON RESEARCH. To assess efficacy against CEW, each plant received 5 second-instar CEW larvae on the silks of ears on 2012/08/21 during flowering (principal growth stage #6). On 2012/09/04, ears were examined for live larvae and feeding damage, determined according to the criteria listed in Table 8.

TABLE 8

Criteria for corn earworm damage assessment.

| Score | Criterion |
|---|---|
| 0 | No damage to silks, husks, cob tip, or kernels |
| 1 | Slight damage to silks or husks only; No cob tip damage or kernels consumed |
| 2 | Moderate damage to silks or husks only; No cob tip damage or kernels consumed |
| 3 | Moderate damage to silks or husks; Slight damage to cob tips, No kernels consumed |
| 4 | Moderate damage to silks, husks, cob tips; Slight damage to kernels, 0.1 to 1.0 cm kernel area consumed (<2 kernels) |
| 5 | Moderate damage to silks, husks, cob tips; Moderate damage to kernels, >1.0 to 2.0 cm of kernel area consumed (3 to 5 kernels) |
| 6 | Heavy damage to silks, husks, cob tips; Moderate damage to kernels, >2.0 to 4.0 cm of kernel area consumed (6 to 10 kernels) |
| 7 | Heavy damage to silks, husks, cob tips; Heavy damage to kernels, >4.0 to 6.0 cm of kernel area consumed (11 to 15 kernels) |
| 8 | Severe damage to silks, husks, cob tips, possibly multiple ear entry locations; Severe damage to kernels, >6.0 to 10.0 cm of kernel area consumed (16 to 25 kernels) |

Quantitative Enzyme Linked Immunosorbant Assays (ELISA) using standard protocols were used to evaluate Cry1Da leaf protein levels in each event. The ELISAs were performed using multiple dilutions of plant extracts and using reagents and instructions essentially as provided by ELISA kit suppliers. Cry1Da antibody as described above was used.

TABLE 9

Results of analytical and insect feeding tests on field-grown plants. Means were separated by the Tukey-Kramer HSD test.

| | | CEW | | | |
|---|---|---|---|---|---|
| Plant ID | Leaf Cry1Da (ng/cm$^2$) | No. of Kernels Consumed per Ear | Number of Insects per Ear | Ear Feeding Scale | FAW Foliar Damage |
| B104/pDAB109841 {2}021.001 | 135.20 (A)* | 0.36 (C) | 0.08 (C) | 1.28 (C)(D) | 3.90 (B)(C) |
| B104/pDAB109841 {3} 108.001 | 135.13 (A) | 0.00 (C) | 0.00 (C) | 1.00 (D) | 2.00 (D) |
| B104/pDAB109841 {1} 189.001 | 134.75 (A) | 5.15 (C) | 0.29 (C) | 1.97 (C)(D) | 3.80 (B)(C)(D) |
| B104/pDAB109841 {1} 188.001 | 122.15 (A)(B) | 0.00 (C) | 0.05 (C) | 1.03 (D) | 3.40 (B)(C)(D) |
| B104/pDAB109841 {3}116.001 | 107.53 (A)(B)(C) | 0.11 (C) | 0.22 (C) | 1.19 (C)(D) | 2.80 (B)(C)(D) |
| B104/pDAB109841 {1}187.001 | 103.20 (A)(B)(C) | 5.16 (C) | 0.32 (C) | 2.03 (C)(D) | 4.16 (B)(C) |
| B104/pDAB109841 {1}183.001 | 89.58 (B)(C) | 1.62 (C) | 0.08 (C) | 1.42 (C)(D) | 4.07 (B)(C) |
| B104/pDAB109841 {1}185.001 | 67.95 (C) | 0.00 (C) | 0.03 (C) | 1.00 (D) | 4.45 (B) |
| Negative Control Plants | | | | | |
| Null (B104) | N/A | 32.46 (B) | 1.26 (B) | 5.57 (B) | 7.95 (A) |

*Levels not connected by same letter are significantly different.
** N/A = Not Applicable There was a broad range of Cry1Da accumulation levels, from 67 ng/cm to 135 ng/cm$^2$ All of the pDAB 109841 events tested provided a statistically similar level of protection against CEW, at both the kernel consumption and ear infestation levels, regardless of Cry1Da production level.

REFERENCES

Frankenhuyzen, K. 2009. Minireview: Insecticidal activity of *Bacillus thuringiensis* crystal proteins. Journal of Invertebrate Pathology. 101:1-16.

Karim S., Ridzuddin, S., Gould, F., Dean, D. H. 2000. Determination of Receptor Binding Properties of *Bacillus thuringiensis* δ-Endotoxins to Cotton Bollworm (*Helicoverpa zea*) and Pink Bollworm (*Pectinophora gossypiella*) Midgut Brush Border Membrane Vesicles. Pesticide Biochemistry and Physiology 67(3): 198-216.

Hate, H., P. Soetaert, S. Jansens, and M. Peferoen. 1990. Nucleotide sequence and deduced amino acid sequence of a new Lepidoptera-specific crystal protein gene from *Bacillus thuringiensis*. Nucl. Acids Res. 18:5545.

Payne, J., and A. J. Sick. 1997. U.S. Pat. No. 5,691,308.

The invention claimed is:

1. A method of controlling corn earworm damage to plants, said method comprising providing one or more plants expressing a Cry1Da insecticidal protein to said corn earworm for ingestion, wherein the Cry1Da insecticidal protein comprises SEQ ID NO: 6 and wherein each of the plants further comprises at least one additional input trait.

2. The method of claim 1, wherein each of the plants further comprises at least one insect resistance trait, at least one herbicide tolerance trait, or a combination of at least one insect resistance trait and at least one additional herbicide tolerance trait.

3. The method of claim 1, wherein the at least one additional input trait comprises an insect resistance trait.

4. The method of claim 3, wherein the insect resistance trait is conferred by an insecticidal protein.

5. The method of claim 3, wherein the insect resistance trait is conferred by a B.t.-derived insecticidal protein other than a Cry1Da insecticidal protein.

6. The method of claim 3, wherein the insect resistance trait is conferred by RNAi.

7. The method of claim 1, wherein the at least one additional input trait comprises a herbicide tolerance trait.

8. The method of claim 7, wherein the herbicide tolerance trait provides tolerance to one or more herbicides selected from the group of (i) Acetolactate Synthase (ALS) inhibitors; (ii) Glutamine Synthetase (GS) inhibitors; (iii) 4-HydroxyPhenylPyruvate Dioxygenase (HPPD) inhibitors; (iv) 5-EnolPyruvylShikimate-3-Phosphate Synthase (EPSPS) inhibitors, and (v) Acetyl-Coenzyme A Carboxylase (ACCase) inhibitors.

9. The method of claim 7, wherein the herbicide tolerance trait provides tolerance to one or more herbicides selected from the group of phenoxy acids herbicides, pyridyloxyacetates auxin herbicides, phenoxy acids herbicides, and aryloxyphenoxypropionate herbicides.

10. The method of claim 7, wherein the herbicide tolerance trait provides tolerance to glyphosate.

11. The method of claim 7, wherein the herbicide tolerance trait provides tolerance to aryloxyphenoxypropionate.

12. The method of claim 7, wherein the herbicide tolerance trait provides tolerance to haloxyfop.

13. The method of claim 7, wherein the herbicide tolerance trait is conferred by AAD-1 herbicide tolerance protein.

14. The method of claim 1, wherein expression of Cry1Da is controlled by a maize ubiquitin promoter.

* * * * *

SEQUENCE LISTING

```
<160> NUMBER OF SEQ ID NOS: 15

<210> SEQ ID NO 1
<211> LENGTH: 3420
<212> TYPE: DNA
<213> ORGANISM: artificial
<220> FEATURE:
<223> OTHER INFORMATION: DIG-911 DNA; Cry1Da2/Cry1Ab chimeric toxin,
      from pDOW2848

<400> SEQUENCE: 1
atggaaataa ataatcaaaa ccaatgtgtg ccttacaatt gtttaagtaa tcctaaggag     60
ataatattag gcgaggaaag gctagaaaca gggaatactg tagcagacat ttcattaggg    120
```

```
cttattaatt ttctatattc taattttgta ccaggaggag gatttatagt aggtttacta    180
gaattaatat ggggatttat agggccttcg caatgggata ttttttttagc tcaaattgag   240 caattgatta gtcaaagaat agaagaattt gctaggaatc aggcaatttc aagattggag   300
gggctaagca atctttataa ggtctatgtt agagcgttta gcgactggga gaaagatcct   360
actaatcctg ctttaaggga agaaatgcgt atacaattta atgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgttttttcc aaattatgat attagaacat atccaattca aacagctact   780
cagctaacga gggaagtcta tctggattta ccttttatta atgaaaatct ttctcctgca   840
gcaagctatc caacctttc agctgctgaa agtgctataa ttagaagtcc tcatttagta   900 gacttttaa atagctttac catttataca gatagtctgg cacgttatgc atattgggga   960
gggcacttgg taaattcttt ccgcacagga accactacta atttgataag atcccctta  1020 tatggaaggg aaggaaatac agagcgcccc gtaactatta ccgcatcacc tagcgtacca  1080
atatttagaa cactttcata tattacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac attttttagaa cggattagtg gaccaagaat agcaggcacc  1320
gtattttctt ggacacaccg tagtgccagc cctactaatg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500 cgagtaaccct tcacaggaag attaccacaa agttattata tacgtttccg ttatgcttcg  1560
gtagcaaata ggagtggtac atttagatat tcacagccac cttcgtatgg aatttcatttt  1620 ccaaaaacta tggacgcagg tgaaccacta acatctcgtt cgttcgctca tacaacactc  1680
ttcactccaa taaccttttc acgagctcaa gaagaatttg atctatacat ccaatcgggt  1740
gtttatatag atcgaattga atttataccg gttactgcaa cactggaggc agagtctgac  1800
ttggaaagag cacagaaggc ggtgaatgct ctgttcactt cgtccaatca gattgggctc  1860
aagacagatg tgactgacta tcacatcgat cgcgtttcca accttgttga gtgcctctct  1920
gatgagttct gtttggatga agaaggag ttgtccgaga aggtcaaaca tgctaagcga  1980
cttagtgatg agcggaactt gcttcaagat cccaactttc gcgggatcaa caggcaacta  2040
gatcgtggat ggaggggaag tacgacatc accattcaag gaggtgatga tgtgttcaag  2100
gagaactatg ttacgctctt gggtaccttt gatgagtgct atccaacata cctgtaccag  2160
aagatagatg aatcgaaact caaagcctac acaagatacc agttgagagg ttacatcgag  2220
gacagtcaag accttgagat ctacctcatc agatacaacg ccaaacatga gacagtcaat  2280
gtgcctggga cgggttcact ctggccactt tcagccccaa gtcccatcgg caagtgtgcc  2340
catcactcac accacttctc cttggacata gacgttggct gtaccgacct gaacgaagac  2400
ctcggtgtgt gggtgatctt caagatcaag actcaagatg gccatgccag gctaggcaat  2460
ctggagtttc tagaagagaa accacttgtt ggagaagccc tcgctagagt gaagagggct  2520
```

-continued

```
gagaagaagt ggagggacaa gagagagaag ttggaatggg aaacaaacat tgtgtacaaa    2580
gaagccaaag aaagcgttga cgctctgttt gtgaactctc agtatgatag gctccaagct    2640
gataccaaca tagctatgat tcatgctgca gacaaacgcg ttcatagcat tcgggaagct    2700
taccttcctg aacttagcgt gattccgggt gtcaatgctg ctatctttga agagttagaa    2760
gggcgcatct tcactgcatt ctccttgtat gatgcgagga atgtcatcaa gaatggtgac    2820
ttcaacaatg gccatatcctg ctggaatgtg aaagggcacg tagatgtaga agaacagaac    2880
aatcaccgct ctgtccttgt tgttcctgag tgggaagcag aagtttcaca agaagttcgt    2940
gtctgtcctg gtcgtggcta cattcttcgt gttaccgcgt acaaagaagg atacggagaa    3000
ggttgcgtca ccatacacga gattgagaac aacaccgacg agctgaagtt cagcaactgc    3060
gtcgaggagg aagtctaccc aaacaacacc gtaacttgca atgactacac tgcgactcaa    3120
gaggagtatg agggtactta cacttctcgc aatcgaggat acgatggagc ctatgagagc    3180
aactcttctg tacccgctga ctatgcatca gcctatgagg agaaggctta caccgatgga    3240
cgtagggaca tccttgcga atctaacaga ggctatgggg actacacacc gttaccagcc    3300
ggctatgtca ccaaagagtt agagtacttt ccagaaaccg acaaggtttg gattgagatt    3360
ggagaaacgg aaggaacatt cattgttgat agcgtggagt tacttctgat ggaggaatga    3420
```

<210> SEQ ID NO 2
<211> LENGTH: 1139
<212> TYPE: PRT
<213> ORGANISM: artificial
<220> FEATURE:
<223> OTHER INFORMATION: amino acid sequence for the DIG-911 protein
(Cry1Da2/Cry1Ab chimeric insecticidal toxin, which consists of a
core toxin segment of Cry1Da (amino acids 1 to 594, as disclosed
in GENBANK Accession No. 176415.1 and U.S Patent No. 5,691,308)
and a

<400> SEQUENCE: 2

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
```

-continued

```
            180                 185                 190
Ser Asp Leu Thr Ser Leu Ile His Val Tyr Thr Asn His Cys Val Asp
        195                 200                 205
Thr Tyr Asn Gln Gly Leu Arg Arg Leu Glu Gly Arg Phe Leu Ser Asp
        210                 215                 220
Trp Ile Val Tyr Asn Arg Phe Arg Arg Gln Leu Thr Ile Ser Val Leu
225                 230                 235                 240
Asp Ile Val Ala Phe Phe Pro Asn Tyr Asp Ile Arg Thr Tyr Pro Ile
            245                 250                 255
Gln Thr Ala Thr Gln Leu Thr Arg Glu Val Tyr Leu Asp Leu Pro Phe
        260                 265                 270
Ile Asn Glu Asn Leu Ser Pro Ala Ala Ser Tyr Pro Thr Phe Ser Ala
        275                 280                 285
Ala Glu Ser Ala Ile Ile Arg Ser Pro His Leu Val Asp Phe Leu Asn
        290                 295                 300
Ser Phe Thr Ile Tyr Thr Asp Ser Leu Ala Arg Tyr Ala Tyr Trp Gly
305                 310                 315                 320
Gly His Leu Val Asn Ser Phe Arg Thr Gly Thr Thr Asn Leu Ile
            325                 330                 335
Arg Ser Pro Leu Tyr Gly Arg Glu Gly Asn Thr Glu Arg Pro Val Thr
        340                 345                 350
Ile Thr Ala Ser Pro Ser Val Pro Ile Phe Arg Thr Leu Ser Tyr Ile
        355                 360                 365
Thr Gly Leu Asp Asn Ser Asn Pro Val Ala Gly Ile Glu Gly Val Glu
        370                 375                 380
Phe Gln Asn Thr Ile Ser Arg Ser Ile Tyr Arg Lys Ser Gly Pro Ile
385                 390                 395                 400
Asp Ser Phe Ser Glu Leu Pro Pro Gln Asp Ala Ser Val Ser Pro Ala
            405                 410                 415
Ile Gly Tyr Ser His Arg Leu Cys His Ala Thr Phe Leu Glu Arg Ile
            420                 425                 430
Ser Gly Pro Arg Ile Ala Gly Thr Val Phe Ser Trp Thr His Arg Ser
        435                 440                 445
Ala Ser Pro Thr Asn Glu Val Ser Pro Ser Arg Ile Thr Gln Ile Pro
        450                 455                 460
Trp Val Lys Ala His Thr Leu Ala Ser Gly Ala Ser Val Ile Lys Gly
465                 470                 475                 480
Pro Gly Phe Thr Gly Gly Asp Ile Leu Thr Arg Asn Ser Met Gly Glu
            485                 490                 495
Leu Gly Thr Leu Arg Val Thr Phe Thr Gly Arg Leu Pro Gln Ser Tyr
        500                 505                 510
Tyr Ile Arg Phe Arg Tyr Ala Ser Val Ala Asn Arg Ser Gly Thr Phe
        515                 520                 525
Arg Tyr Ser Gln Pro Pro Ser Tyr Gly Ile Ser Phe Pro Lys Thr Met
        530                 535                 540
Asp Ala Gly Glu Pro Leu Thr Ser Arg Ser Phe Ala His Thr Thr Leu
545                 550                 555                 560
Phe Thr Pro Ile Thr Phe Ser Arg Ala Gln Glu Glu Phe Asp Leu Tyr
            565                 570                 575
Ile Gln Ser Gly Val Tyr Ile Asp Arg Ile Glu Phe Ile Pro Val Thr
            580                 585                 590
Ala Thr Leu Glu Ala Glu Ser Asp Leu Glu Arg Ala Gln Lys Ala Val
        595                 600                 605
```

```
Asn Ala Leu Phe Thr Ser Ser Asn Gln Ile Gly Leu Lys Thr Asp Val
    610                 615                 620

Thr Asp Tyr His Ile Asp Arg Val Ser Asn Leu Val Glu Cys Leu Ser
625                 630                 635                 640

Asp Glu Phe Cys Leu Asp Glu Lys Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Leu Asp Arg Gly Trp Arg Gly Ser Thr
        675                 680                 685

Asp Ile Thr Ile Gln Gly Gly Asp Val Phe Lys Glu Asn Tyr Val
    690                 695                 700

Thr Leu Leu Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Thr Val Asn Val Pro Gly Thr Gly Ser Leu Trp
        755                 760                 765

Pro Leu Ser Ala Pro Ser Pro Ile Gly Lys Cys Ala His His Ser His
    770                 775                 780

His Phe Ser Leu Asp Ile Asp Val Gly Cys Thr Asp Leu Asn Glu Asp
785                 790                 795                 800

Leu Gly Val Trp Val Ile Phe Lys Ile Lys Thr Gln Asp Gly His Ala
                805                 810                 815

Arg Leu Gly Asn Leu Glu Phe Leu Glu Glu Lys Pro Leu Val Gly Glu
            820                 825                 830

Ala Leu Ala Arg Val Lys Arg Ala Glu Lys Lys Trp Arg Asp Lys Arg
        835                 840                 845

Glu Lys Leu Glu Trp Glu Thr Asn Ile Val Tyr Lys Glu Ala Lys Glu
    850                 855                 860

Ser Val Asp Ala Leu Phe Val Asn Ser Gln Tyr Asp Arg Leu Gln Ala
865                 870                 875                 880

Asp Thr Asn Ile Ala Met Ile His Ala Ala Asp Lys Arg Val His Ser
                885                 890                 895

Ile Arg Glu Ala Tyr Leu Pro Glu Leu Ser Val Ile Pro Gly Val Asn
            900                 905                 910

Ala Ala Ile Phe Glu Glu Leu Glu Gly Arg Ile Phe Thr Ala Phe Ser
        915                 920                 925

Leu Tyr Asp Ala Arg Asn Val Ile Lys Asn Gly Asp Phe Asn Asn Gly
    930                 935                 940

Leu Ser Cys Trp Asn Val Lys Gly His Val Asp Val Glu Glu Gln Asn
945                 950                 955                 960

Asn His Arg Ser Val Leu Val Pro Glu Trp Glu Ala Glu Val Ser
                965                 970                 975

Gln Glu Val Arg Val Cys Pro Gly Arg Gly Tyr Ile Leu Arg Val Thr
            980                 985                 990

Ala Tyr Lys Glu Gly Tyr Gly Glu  Gly Cys Val Thr Ile  His Glu Ile
        995                 1000                 1005

Glu Asn  Asn Thr Asp Glu Leu  Lys Phe Ser Asn Cys  Val Glu Glu
    1010                 1015                 1020
```

-continued

| | | | | | | | | | | | |
|---|---|---|---|---|---|---|---|---|---|---|---|
|Glu|Val|Tyr|Pro|Asn|Asn|Thr|Val|Thr|Cys|Asn|Asp|Tyr|Thr|Ala|
| |1025| | | |1030| | | |1035| | | | | |

Thr Gln Glu Glu Tyr Glu Gly Thr Tyr Thr Ser Arg Asn Arg Gly
    1040            1045            1050

Tyr Asp Gly Ala Tyr Glu Ser Asn Ser Ser Val Pro Ala Asp Tyr
    1055            1060            1065

Ala Ser Ala Tyr Glu Glu Lys Ala Tyr Thr Asp Gly Arg Arg Asp
    1070            1075            1080

Asn Pro Cys Glu Ser Asn Arg Gly Tyr Gly Asp Tyr Thr Pro Leu
    1085            1090            1095

Pro Ala Gly Tyr Val Thr Lys Glu Leu Glu Tyr Phe Pro Glu Thr
    1100            1105            1110

Asp Lys Val Trp Ile Glu Ile Gly Glu Thr Glu Gly Thr Phe Ile
    1115            1120            1125

Val Asp Ser Val Glu Leu Leu Leu Met Glu Glu
    1130            1135

<210> SEQ ID NO 3
<211> LENGTH: 3447
<212> TYPE: DNA
<213> ORGANISM: artificial
<220> FEATURE:
<223> OTHER INFORMATION: DIG-180 DNA; Cry1Fa2

<400> SEQUENCE: 3

```
atggaaaata atattcaaaa tcaatgcgta ccttacaatt gtttaaataa tcctgaagta      60
gaaatactga acgaagaacg cagcaccggc cgcctgccgc tggacatcag cctgagcctt     120
acacgtttcc ttttgagtga atttgttcca ggtgtgggag ttgcgtttgg attatttgat     180
ttaatatggg gttttataac tccttctgat tggagcttat ttcttttaca gattgaacaa     240
ttgattgagc aaagaataga acattggaa ggaaccggg caattactac attacgaggg     300
ttagcagata gctatgaaat ttatattgaa gcactaagag agtgggaagc aaatcctaat     360
aatgcacaat taagggaaga tgtgcgtatt cgatttgcta atacagacga cgctttaata     420
acagcaataa ataattttac acttacaagt tttgaaatcc ctctttttatc ggtctatgtt     480
caagcggcga atttacattt atcactatta agagacgcag tatcgtttgg gcagggttgg     540
ggactggata tagctactgt taataatcat tataatagat aataaatct tattcataga     600
tatacgaaac attgtttgga cacatacaat caaggattag aaaacttaag aggtactaat     660
actcgacaat gggcaagatt caatcagttt aggagagatt taacacttac tgtattagat     720
atcgttgctc ttttttccgaa ctacgatgtt agaacatatc caattcaaac gtcatcccaa     780
ttaacaaggg aaatttatac aagttcagta attgaggatt ctccagtttc tgctaatata     840
cctaatggtt ttaatagggc ggaatttgga gttagaccgc cccatcttat ggactttatg     900
aattctttgt ttgtaactgc agagactgtt agaagtcaaa ctgtgtgggg aggacactta     960
gttagttcac gaaatacggc tggtaaccgt ataaatttcc ctagttacgg ggtcttcaat    1020
cctggtggcg ccatttggat tgcagatgag gatccacgtc tttttatcg gacattatca    1080
gatcctgttt tgtccgagg aggatttggg aatcctcatt atgtactggg gcttagggga    1140
gtagcatttc aacaaactgg tacgaaccac acccgaacat ttagaaatag tgggaccata    1200
gattctctag atgaaatccc acctcaggat aatagtgggg caccttggaa tgattatagt    1260
catgtattaa atcatgttac atttgtacga tggccaggtg agatttcagg aagtgattca    1320
tggagagctc caatgttttc ttggacgcac cgtagtgcaa cccctacaaa tacaattgat    1380
```

```
ccggagagga ttactcaaat accattggta aaagcacata cacttcagtc aggtactact    1440
gttgtaagag ggcccggggtt tacgggagga gatattcttc gacgaacaag tggaggacca   1500
tttgcttata ctattgttaa tataaatggg caattacccc aaaggtatcg tgcaagaata    1560
cgctatgcct ctactacaaa tctaagaatt tacgtaacgg ttgcaggtga acggattttt    1620
gctggtcaat ttaacaaaac aatggatacc ggtgacccat taacattcca atcttttagt    1680
tacgcaacta ttaatacagc ttttacattc ccaatgagcc agagtagttt cacagtaggt    1740
gctgatactt ttagttcagg gaatgaagtt tatatagaca gatttgaatt gattccagtt    1800
actgcaacat tggaagcaga atctgattta gaaagagcac aaaaggcggt gaatgcgctg    1860
tttacttcta gcaaccaaat agggctaaaa acagatgtga cggattatca tatcgatcga    1920
gtatccaatt tagttgagtg tttatctgat gaattttgtc tggatgaaaa aaaagaattg    1980
tccgagaaag tcaaacatgc gaagcgactt agtgatgagc ggaatttact tcaagatcca    2040
aactttagag ggatcaatag acaactagac cgtggctgga gaggaagtac ggatattacc    2100
atccaaggag gcgatgacgt attcaaagag aattacgtta cgctattggg tacctttgat    2160
gagtgctatc caacgtattt atatcaaaaa atagatgagt cgaaattaaa agcctatacc    2220
cgttaccaat taagagggta tatcgaagat agtcaagact tagaaatcta tttaattcgc    2280
tacaatgcca acacgaaaac agtaaatgtg ccaggtacgg gttccttatg ccgctttca    2340 gccccaagtc aatcggaaa atgtgcccat cattcccatc atttctcctt ggacattgat    2400
gttggatgta cagacttaaa tgaggactta ggtgtatggg tgatattcaa gattaagacg    2460
caagatggcc atgcaagact aggaaatcta gaatttctcg aagagaaacc attagtagga    2520
gaagcactag ctcgtgtgaa aagagcggag aaaaaatgga gagacaaacg tgaaaaattg    2580
gaatgggaaa caaatattgt ttataaagag gcaaaagaat ctgtagatgc tttatttgta    2640
aactctcaat atgatagatt acaagcggat accaacatcg cgatgattca tgcggcagat    2700
aaacgcgttc atagcattcg agaagcttat ctgcctgagc tgtctgtgat tccgggtgtc    2760
aatgcggcta ttttttgaaga attagaaggg cgtatttcca ctgcattctc cctatatgat    2820
gcgagaaatg tcattaaaaa tggtgatttt aataatggct tatcctgctg gaacgtgaaa    2880
gggcatgtag atgtagaaga acaaaacaac caccgttcgg tccttgttgt tccggaatgg    2940
gaagcagaag tgtcacaaga agttcgtgtc tgtccgggtc gtggctatat ccttcgtgtc    3000
acagcgtaca aggagggata tggagaaggt tgcgtaacca ttcatgagat cgagaacaat    3060
acagacgaac tgaagtttag caactgtgta gaagaggaag tatatccaaa caacacggta    3120
acgtgtaatg attatactgc gactcaagaa gaatatgagg gtacgtacac ttctcgtaat    3180
cgaggatatg acgagccta tgaaagcaat tcttctgtac cagctgatta tgcatcagcc    3240
tatgaagaaa aagcatatac agatggacga agagacaatc cttgtgaatc taacagagga    3300 tatgggatt acacaccact accagctggc tatgtgacaa agaattaga gtacttccca    3360 gaaaccgata aggtatggat tgagatcgga gaaacggaag gaacattcat cgtggacagc    3420
gtggaattac ttcttatgga ggaataa                                        3447
```

<210> SEQ ID NO 4
<211> LENGTH: 1148
<212> TYPE: PRT
<213> ORGANISM: artificial
<220> FEATURE:
<223> OTHER INFORMATION: DIG-180 protein; Cry1Fa2

```
<400> SEQUENCE: 4

Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415
```

```
Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
            450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
            515                 520                 525

Arg Ile Tyr Val Thr Val Ala Gly Glu Arg Ile Phe Ala Gly Gln Phe
            530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Leu Glu Ala Glu Ser
            595                 600                 605

Asp Leu Glu Arg Ala Gln Lys Ala Val Asn Ala Leu Phe Thr Ser Ser
            610                 615                 620

Asn Gln Ile Gly Leu Lys Thr Asp Val Thr Asp Tyr His Ile Asp Arg
625                 630                 635                 640

Val Ser Asn Leu Val Glu Cys Leu Ser Asp Glu Phe Cys Leu Asp Glu
                645                 650                 655

Lys Lys Glu Leu Ser Glu Lys Val Lys His Ala Lys Arg Leu Ser Asp
            660                 665                 670

Glu Arg Asn Leu Leu Gln Asp Pro Asn Phe Arg Gly Ile Asn Arg Gln
            675                 680                 685

Leu Asp Arg Gly Trp Arg Gly Ser Thr Asp Ile Thr Ile Gln Gly Gly
            690                 695                 700

Asp Asp Val Phe Lys Glu Asn Tyr Val Thr Leu Leu Gly Thr Phe Asp
705                 710                 715                 720

Glu Cys Tyr Pro Thr Tyr Leu Tyr Gln Lys Ile Asp Glu Ser Lys Leu
            725                 730                 735

Lys Ala Tyr Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
            755                 760                 765

Asn Val Pro Gly Thr Gly Ser Leu Trp Pro Leu Ser Ala Pro Ser Pro
            770                 775                 780

Ile Gly Lys Cys Ala His His Ser His His Phe Ser Leu Asp Ile Asp
785                 790                 795                 800

Val Gly Cys Thr Asp Leu Asn Glu Asp Leu Gly Val Trp Val Ile Phe
                805                 810                 815

Lys Ile Lys Thr Gln Asp Gly His Ala Arg Leu Gly Asn Leu Glu Phe
            820                 825                 830
```

```
Leu Glu Glu Lys Pro Leu Val Gly Glu Ala Leu Ala Arg Val Lys Arg
        835                 840                 845

Ala Glu Lys Lys Trp Arg Asp Lys Arg Glu Lys Leu Glu Trp Glu Thr
850                 855                 860

Asn Ile Val Tyr Lys Glu Ala Lys Glu Ser Val Asp Ala Leu Phe Val
865                 870                 875                 880

Asn Ser Gln Tyr Asp Arg Leu Gln Ala Asp Thr Asn Ile Ala Met Ile
            885                 890                 895

His Ala Ala Asp Lys Arg Val His Ser Ile Arg Glu Ala Tyr Leu Pro
            900                 905                 910

Glu Leu Ser Val Ile Pro Gly Val Asn Ala Ala Ile Phe Glu Glu Leu
        915                 920                 925

Glu Gly Arg Ile Phe Thr Ala Phe Ser Leu Tyr Asp Ala Arg Asn Val
    930                 935                 940

Ile Lys Asn Gly Asp Phe Asn Asn Gly Leu Ser Cys Trp Asn Val Lys
945                 950                 955                 960

Gly His Val Asp Val Glu Glu Gln Asn Asn His Arg Ser Val Leu Val
            965                 970                 975

Val Pro Glu Trp Glu Ala Glu Val Ser Gln Glu Val Arg Val Cys Pro
        980                 985                 990

Gly Arg Gly Tyr Ile Leu Arg Val Thr Ala Tyr Lys Glu Gly Tyr Gly
        995                 1000                1005

Glu Gly Cys Val Thr Ile His Glu Ile Glu Asn Asn Thr Asp Glu
    1010                1015                1020

Leu Lys Phe Ser Asn Cys Val Glu Glu Glu Val Tyr Pro Asn Asn
    1025                1030                1035

Thr Val Thr Cys Asn Asp Tyr Thr Ala Thr Gln Glu Glu Tyr Glu
    1040                1045                1050

Gly Thr Tyr Thr Ser Arg Asn Arg Gly Tyr Asp Gly Ala Tyr Glu
    1055                1060                1065

Ser Asn Ser Ser Val Pro Ala Asp Tyr Ala Ser Ala Tyr Glu Glu
    1070                1075                1080

Lys Ala Tyr Thr Asp Gly Arg Arg Asp Asn Pro Cys Glu Ser Asn
    1085                1090                1095

Arg Gly Tyr Gly Asp Tyr Thr Pro Leu Pro Ala Gly Tyr Val Thr
    1100                1105                1110

Lys Glu Leu Glu Tyr Phe Pro Glu Thr Asp Lys Val Trp Ile Glu
    1115                1120                1125

Ile Gly Glu Thr Glu Gly Thr Phe Ile Val Asp Ser Val Glu Leu
    1130                1135                1140

Leu Leu Met Glu Glu
    1145

<210> SEQ ID NO 5
<211> LENGTH: 1812
<212> TYPE: DNA
<213> ORGANISM: artificial
<220> FEATURE:
<223> OTHER INFORMATION: Cry1Da2 v4 DNA from pDAB109841 (truncated
      Cry1Da; maize optimized)

<400> SEQUENCE: 5
atggagatca acaaccagaa tcagtgcgtt ccttacaact gtctgagcaa ccccaaagaa      60
atcatccttg gcgaggagag gctggaaact ggcaacacag tggctgacat tagcttgggt     120
cttatcaact tcttgtactc aaactttgtt cccggtggag gcttcattgt gggactgctt     180
```

-continued

```
gagctgatat ggggtttcat aggtccgagc cagtgggaca tctttctggc acaaatcgag    240
cagctcatct cacagcggat tgaggagttt gcgagaaatc aagccatatc gagactcgaa    300
gggctgtcca acttgtacaa ggtctatgtg agggctttct ctgattggga gaaggacccc    360
acgaatccag cgcttcgcga ggagatgagg atacagttca atgacatgaa ctctgcgttg    420
atcacggcta ttccgctctt tagggtgcag aactacgagg ttgctctgct ctcagtgtac    480
gtgcaagctg ccaacttgca tctgagcatc ctccgggacg tctcggtgtt tggggaacgg    540
tggggttatg acaccgcaac gatcaacaac cgctattcag accttacatc tcttatccac    600
gtgtacacga atcactgcgt tgatacgtac aatcaaggcc tccgcagact cgaagggagg    660
ttcctcagcg attggattgt ttacaatcgc ttcagacggc aactcacaat ctcggttctg    720
gacatagtcg cgttcttccc gaactatgat atccgcacct atcccattca gaccgctact    780
cagctcactc gcgaagtgta tcttgacctc ccgttcatca atgagaactt gtcaccagca    840
gcgtcctatc ccaccttctc agctgcggag tccgctatca tccgctcccc acatctggtt    900
gatttcctca actctttcac tatctacacc gactcgcttg cgagatacgc atactggggt    960
ggccatctgg tgaactcatt ccggactggc accacgacca atctgatccg cagccctctc   1020
tacggacgcg agggcaacac cgagaggcca gtgaccatca ccgcttcccc ttccgttcct   1080
atcttccgca ccctttcgta cattactggc ctcgacaaca gcaacccagt cgctggcatc   1140
gagggtgttg agtttcagaa caccatttct aggtctatct ataggaagag cggtccaata   1200
gactcgtttt ctgagttgcc tccccaagat gcctctgtca gcccagccat tggctactcc   1260
catcggctct gtcacgccac cttccttgaa cgcatctccg gaccaaggat cgctgggacg   1320
gtctttagct ggacccaccg ctcagcatct ccgacaaatg aggtctcccc ttcccgcatc   1380
acacaaatcc cgtgggtgaa ggcacacaca ttggcctcgg gagcctcggt catcaaaggg   1440
cctggcttca ctggaggcga cattctgacg aggaactcaa tgggtgagct ggggaccttg   1500
agggtcactt tcactggacg cctcccacag tcctactaca ttcggttccg ctatgccagc   1560
gtggccaata ggtccggaac attccgctac agccagccac ccagctacgg cattagcttc   1620
cctaagacta tggatgctgg ggaacctctg acctcaaggt cgtttgccca cacgacgctg   1680
ttcaccccta tcacattcag cagagcacaa gaggagtttg atctgtacat ccagtccgga   1740
gtctacattg accggatcga gttcattccg gttactgcga cactcgaggc tgaatcggat   1800
cttgaaaggt ga                                                       1812
```

```
<210> SEQ ID NO 6
<211> LENGTH: 603
<212> TYPE: PRT
<213> ORGANISM: artificial
<220> FEATURE:
<223> OTHER INFORMATION: Cry1Da2 v4 protein (truncated Cry1Da)

<400> SEQUENCE: 6

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60
```

-continued

```
Gly Phe Ile Gly Pro Ser Gln Trp Asp Ile Phe Leu Ala Gln Ile Glu
 65                  70                  75                  80

Gln Leu Ile Ser Gln Arg Ile Glu Glu Phe Ala Arg Asn Gln Ala Ile
                 85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
        355                 360                 365

Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
```

-continued

```
                    485                 490                 495
Leu Gly Thr Leu Arg Val Thr Phe Thr Gly Arg Leu Pro Gln Ser Tyr
                500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
        530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
            580                 585                 590

Ala Thr Leu Glu Ala Glu Ser Asp Leu Glu Arg
        595                 600

<210> SEQ ID NO 7
<211> LENGTH: 20
<212> TYPE: DNA
<213> ORGANISM: artificial
<220> FEATURE:
<223> OTHER INFORMATION: AAD1F Primer

<400> SEQUENCE: 7
tgttcggttc cctctaccaa                                               20

<210> SEQ ID NO 8
<211> LENGTH: 22
<212> TYPE: DNA
<213> ORGANISM: artificial
<220> FEATURE:
<223> OTHER INFORMATION: AAD1R Primer

<400> SEQUENCE: 8
caacatccat caccttgact ga                                            22

<210> SEQ ID NO 9
<211> LENGTH: 24
<212> TYPE: DNA
<213> ORGANISM: artificial
<220> FEATURE:
<223> OTHER INFORMATION: AAD1P Probe

<400> SEQUENCE: 9
cacagaaccg tcgcttcagc aaca                                          24

<210> SEQ ID NO 10
<211> LENGTH: 19
<212> TYPE: DNA
<213> ORGANISM: artificial
<220> FEATURE:
<223> OTHER INFORMATION: SPC1A Primer

<400> SEQUENCE: 10
cttagctgga taacgccac                                                19

<210> SEQ ID NO 11
<211> LENGTH: 19
<212> TYPE: DNA
<213> ORGANISM: artificial
<220> FEATURE:
<223> OTHER INFORMATION: SPC1S Primer
```

```
<400> SEQUENCE: 11
gaccgtaagg cttgatgaa                                              19

<210> SEQ ID NO 12
<211> LENGTH: 21
<212> TYPE: DNA
<213> ORGANISM: artificial
<220> FEATURE:
<223> OTHER INFORMATION: TQSPC Probe

<400> SEQUENCE: 12
cgagattctc cgcgctgtag a                                           21

<210> SEQ ID NO 13
<211> LENGTH: 18
<212> TYPE: DNA
<213> ORGANISM: artificial
<220> FEATURE:
<223> OTHER INFORMATION: InvertaseF Primer

<400> SEQUENCE: 13
tggcggacga cgacttgt                                               18

<210> SEQ ID NO 14
<211> LENGTH: 19
<212> TYPE: DNA
<213> ORGANISM: artificial
<220> FEATURE:
<223> OTHER INFORMATION: InvertaseR Primer

<400> SEQUENCE: 14
aaagtttgga ggctgccgt                                              19

<210> SEQ ID NO 15
<211> LENGTH: 21
<212> TYPE: DNA
<213> ORGANISM: artificial
<220> FEATURE:
<223> OTHER INFORMATION: InvertaseP Probe

<400> SEQUENCE: 15
cgagcagacc gccgtgtact t                                           21
```